United States Patent
Greaves et al.

(10) Patent No.: US 7,744,657 B2
(45) Date of Patent: Jun. 29, 2010

(54) STYRL TETRAHYDROQUINOLINIUM THIOL/DISULFIDE DYE COMPOUND AND METHOD FOR LIGHTENING KERATIN MATERIALS USING THE SAME

(75) Inventors: Andrew Greaves, Montevrain (FR); Nicolas Daubresse, la Celles St Cloud (FR); Franco Manfre, le Perreux sur Marne (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/234,135

(22) Filed: Sep. 19, 2008

(65) Prior Publication Data

US 2009/0126125 A1    May 21, 2009

Related U.S. Application Data

(60) Provisional application No. 60/960,678, filed on Oct. 10, 2007.

(30) Foreign Application Priority Data

Sep. 21, 2007   (FR) .................................. 07 57753

(51) Int. Cl.
  *A61Q 5/10* (2006.01)
  *C07C 321/00* (2006.01)
(52) U.S. Cl. ....................... 8/405; 8/431; 8/465; 8/568; 8/587; 8/648; 562/426
(58) Field of Classification Search ..................... 8/405, 8/431, 465, 568, 587, 648; 562/426
See application file for complete search history.

(56) References Cited

U.S. PATENT DOCUMENTS

| | | | |
|---|---|---|---|
| 2,904,385 | A | 9/1959 | Roger et al. |
| 7,147,673 | B2 | 12/2006 | Plos et al. |
| 7,150,764 | B2 | 12/2006 | Plos et al. |
| 7,186,278 | B2 | 3/2007 | Plos et al. |
| 7,192,454 | B2 | 3/2007 | Plos et al. |
| 7,195,650 | B2 | 3/2007 | Plos et al. |
| 7,195,651 | B2 | 3/2007 | Plos et al. |
| 7,198,650 | B2 | 4/2007 | Pourille-Grethen et al. |
| 7,204,860 | B2 | 4/2007 | Plos et al. |
| 7,208,018 | B2 | 4/2007 | Gourlaouen et al. |
| 7,217,296 | B2 | 5/2007 | Pastore et al. |
| 7,250,064 | B2 | 7/2007 | Plos et al. |
| 7,261,744 | B2 | 8/2007 | Gourlaouen et al. |
| 7,276,086 | B2 | 10/2007 | Gourlaouen |
| 7,303,589 | B2 | 12/2007 | Greaves et al. |
| 7,377,946 | B2 | 5/2008 | Gourlaouen et al. |
| 7,488,354 | B2 | 2/2009 | Daubress et al. |
| 7,531,008 | B2 | 5/2009 | Lagrange |
| 7,544,215 | B2 | 6/2009 | Speckbacher et al. |
| 2003/0176316 | A1 | 9/2003 | Whitehead et al. |
| 2004/0253757 | A1 | 12/2004 | Gourlaouen et al. |
| 2005/0031563 | A1 | 2/2005 | Gourlaouen et al. |
| 2007/0231940 | A1 | 10/2007 | Gourlaouen et al. |
| 2009/0049621 | A1 | 2/2009 | Greaves et al. |
| 2009/0089939 | A1 | 4/2009 | Greaves et al. |
| 2009/0126125 | A1 | 5/2009 | Greaves et al. |
| 2009/0126755 | A1 | 5/2009 | Guerin et al. |

FOREIGN PATENT DOCUMENTS

| | | |
|---|---|---|
| BE | 669 934 | 1/1966 |
| EP | 0 860 636 A1 | 8/1998 |
| EP | 1 464 321 A0 | 10/2004 |
| EP | 1 464 323 A1 | 10/2004 |
| EP | 1 464 324 A1 | 10/2004 |
| EP | 1647580 A1 * | 4/2006 |
| EP | 1 792 605 A1 | 6/2007 |
| EP | 2 001 960 A | 12/2008 |
| EP | 2 004 757 A | 12/2008 |
| EP | 2 018 847 A1 | 1/2009 |
| EP | 2 062 945 A2 | 5/2009 |
| FR | 1 156 407 | 5/1958 |
| FR | 2 586 913 A1 | 3/1987 |
| FR | 2 830 189 A1 | 4/2003 |
| FR | 2 830 194 A1 | 4/2003 |
| FR | 2 850 271 A1 | 7/2004 |
| FR | 2 921 381 A1 | 3/2009 |
| FR | 2 921 377 A1 | 6/2009 |
| GB | 2 143 541 A | 2/1985 |
| GB | 2 180 215 A | 3/1987 |

(Continued)

OTHER PUBLICATIONS

STIC Search Report dated Apr. 27, 2009.*
English Abstract of the Patent No. EP 1647580 A1.*
English language abstract of EP 1 464 323 (2004).
English language abstract of EP 2 001 960 (2008).
English language abstract of EP 2 004 757 2008).
English language abstract of EP 2 018 847 (2009).
English language abstract of EP 2 062 945 (2009).
English language abstract of FR 2 850 27 (2004).
English language abstract of WO 2007/110537 (2007).
English language abstract of WO 2007/110539 (2007).
English language abstract of WO 2007/110542 (2007).

(Continued)

*Primary Examiner*—Eisa B Elhilo
(74) *Attorney, Agent, or Firm*—Finnegan, Henderson, Farabow, Garrett & Dunner, L.L.P.

(57) ABSTRACT

The present disclosure relates to the dyeing of keratin materials using thiol/disulfide styryl tetrahydroquinolinium fluorescent dyes. Disclosed herein is a dye composition comprising a thiol/disulfide styryl tetrahydroquinolinium fluorescent dye and a dyeing process with, for instance, a lightening effect on keratin materials such as hair, using said composition. Disclosed herein are thiol fluorescent dyes and the uses thereof in lightening keratin materials. This composition can be used to obtain a lightening effect which can be resistant and visible on dark keratin fibers.

17 Claims, 1 Drawing Sheet

FOREIGN PATENT DOCUMENTS

| WO | WO 96/041173 A1 | 12/1996 |
|---|---|---|
| WO | WO 99/51194 | 10/1999 |
| WO | WO 03/028685 A1 | 4/2003 |
| WO | WO 2004/091473 A2 | 10/2004 |
| WO | WO 2004/091556 A2 | 10/2004 |
| WO | WO 2005/004822 A2 | 1/2005 |
| WO | WO 2005/075574 A1 | 8/2005 |
| WO | WO 2005/097051 A2 | 10/2005 |
| WO | WO 2006/060533 A2 | 6/2006 |
| WO | WO 2006/134043 A2 | 12/2006 |
| WO | WO 2006/136617 A2 | 12/2006 |
| WO | WO 2007/025889 A2 | 3/2007 |
| WO | WO 2007/039527 A2 | 4/2007 |
| WO | WO 2007/110537 A2 | 10/2007 |
| WO | WO 2007/110539 A2 | 10/2007 |
| WO | WO 2007/110542 A2 | 10/2007 |
| WO | WO 2009/037324 A2 | 3/2009 |
| WO | WO 2009/037348 A1 | 3/2009 |
| WO | WO 2009/037350 A2 | 3/2009 |
| WO | WO 2009/037385 A1 | 3/2009 |
| WO | WO 2009/040354 A1 | 4/2009 |
| WO | WO 2009/040355 A2 | 4/2009 |

OTHER PUBLICATIONS

Geoffrey J. Ashwell et al., "Induced rectification from self-assembled monolayers of sterically hindered - bridged chromophores," Journal of Materials Chemistry, Jan. 27, 2005, vol. 15, No. 11, pp. 1160-1166.

Search Report for EP 08 16 4735, dated May 28, 2009.

Search Report for FR 0757753, dated Aug. 4, 2008.

Ashwell, G. et al., "Improved Molecular Rectification from Self-Assembled Monolayers of a Sterically Hindered Dye," Journal of the American Chemical Society, vol. 127, No. 46, (2005), pp. 16238-16244.

Ashwell, G. et al., "Molecular Rectification: Self-Assembled Monolayers of a Donor Acceptor Chromophore Connected via a Truncated Bridge," Journal of Materials Chemistry, vol. 13, No. 12, (2003), pp. 2855-2857.

U.S. Appl. No. 12/233,955, filed Sep. 19, 2008.
U.S. Appl. No. 12/234,001, filed Sep. 19, 2008.
U.S. Appl. No. 12/234,072, filed Sep. 19, 2008.
U.S. Appl. No. 12/282,586, filed Sep. 11, 2008.
U.S. Appl. No. 12/293,684, filed Sep. 19, 2008.
U.S. Appl. No. 12/293,723, filed Sep. 19, 2008.
U.S. Appl. No. 12/293,955, filed Sep. 22, 2008.

English language Abstract of FR 2 921 377, dated Jun. 17, 2009.
English language Abstract of FR 2 921 381, dated Mar. 27, 2009.
French Search Report for FR 07/57755, dated Jul. 30, 2008.
French Search Report for FR 07/57773, dated Jul. 7, 2008.
French Search Report for FR 07/57778, dated Aug. 20, 2008.
International Search Report for PCT/FR2007/050997, dated Jun. 19, 2008.
International Search Report for PCT/FR2007/051003, dated Feb. 19, 2008.
International Search Report for PCT/FR2007/051005, dated May 6, 2008.
International Search Report for PCT/FR2007/051008, dated Feb. 5, 2008.
IP.com document dated Oct. 13, 2005.

Kajikawa, K. et al., "Preparation and Optical Characterization of Hemicyanine Self-Assembled Monolayer on Au Substrate," Molecular Crystals and Liquid Crystals Science and Technology, vol. 370, (2001), pp. 277-283.

Naraokaa, R. et al., "Nonlinear Optical Property of Hemicyanine Self-Assembled Monolayers on Gold and its Absorption Kinetics Probed by Optical Second-Harmonic Generation and Surface Plasmon Resonance Spectroscopy," Chemical Physics Letters, vol. 362, No. 1-2, (2002), pp. 26-30.

Office Action mailed Apr. 28, 2009, in U.S. Appl. No. 12/234,072.

Okawa, H. et al., "Synthesis and Characterization of an Alkanethiol Thin Film Containing a Hemicyanine Dye," Molecular Crystals and Liquid Crystals, vol. 377, (2002), pp. 137-140.

STIC Search Report for U.S. Appl. No. 12/234,072, dated Apr. 23, 2009.

Tsuboi, K. et al., "Formation of Merocyanine Self-Assembled Monolayer and its Nonlinear Optical Properties Probed by Second-Harmonic Generation and Surface Plasmon Resonance," Japanese Journal of Applied Physics, vol. 42, No. 2A, (2003), pp. 607-613.

Wang, Y. et al., "Synthesis and Fluorescence Properties of Triad Compounds with Aromatic Sulfur Bridges," Dyes and Pigments, vol. 51, No. 2-3, (2001), pp. 127-136.

Wang, Y. et al., "Synthesis and Luminescence Properties of Triad Compounds with a Disulfide Bridge," vol. 54, No. 3, (2002), pp. 265-274.

* cited by examiner

FIGURE 1. Curves of reflectance of TH4 locks treated with dyes 1 and 2.
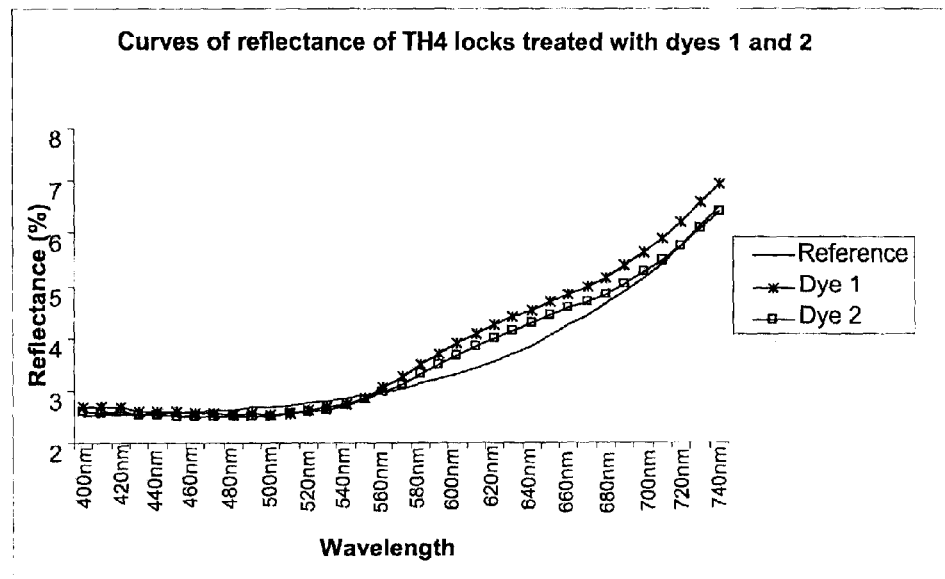

STYRL TETRAHYDROQUINOLINIUM THIOL/DISULFIDE DYE COMPOUND AND METHOD FOR LIGHTENING KERATIN MATERIALS USING THE SAME

This application claims benefit of U.S. Provisional Application No. 60/960,678, filed Oct. 10, 2007, the contents of which are incorporated herein by reference. This application also claims benefit of priority under 35 U.S.C. § 119 to French Patent Application No. FR 0757753, filed Sep. 21, 2007, the contents of which are also incorporated herein by reference.

The present disclosure relates to the dyeing of keratin materials using styryl tetrahydroquinolinium thiol/disulfide fluorescent dyes.

It is well known to dye keratin fibers, for example human keratin fibers, by direct dyeing. The process conventionally used in direct dyeing comprises applying to the keratin fibers direct dyes which are colored or coloring molecules having an affinity for the fibers, allowing them to diffuse and then rinsing the fibers.

The direct dyes which are conventionally used are, for example, dyes of the nitrobenzene type, anthraquinone dyes, nitropyridine dyes, or dyes of the azo, xanthene, acridine, azine, or triarlymethane type.

The coloring of keratin fibers using these conventional direct dyes does not make it possible to significantly lighten keratin fibers.

The lightening of the color of dark keratin fibers to lighter shades, by optionally modifying the shade thereof, constitutes an important demand.

Conventionally, in order to obtain a lighter coloring, a chemical bleaching process is used. This process comprises treating the keratin fibers, such as the hair, with a strong oxidizing system, generally composed of hydrogen peroxide, possibly in combination with persalts, generally in an alkaline medium.

This bleaching system has the drawback of damaging the keratin fibers and of detrimentally affecting their cosmetic properties. The fibers in fact have a tendency to become rough, more difficult to disentangle and more brittle. Finally, the lightening or the bleaching of keratin fibers with oxidizing agents is incompatible with the treatments for modifying the shape of said fibers, such as with hair straightening treatments.

Another lightening technique comprises applying fluorescent direct dyes to dark hair. This technique, described in documents such as International Patent Application Publication Nos. WO 03/028685 and WO 2004/091473, makes it possible to retain the quality of the keratin fiber during the treatment. However, these fluorescent direct dyes do not exhibit satisfactory fastness with respect to outside agents.

In order to increase the fastness of direct colorings, it is known to use disulfide dyes, for instance, imidazolium chromophore dyes described in, for example, International Patent Application Publication No. WO 2005/097051 or European Patent Application Publication No. EP 1647580, or pyridinium/indolinium styryl chromophore dyes described in, for example, International Patent Application Publication Nos. WO 2006/134043 and WO 2006/136617.

The aim of the present disclosure is to provide new systems for dyeing keratin materials, such as human keratin fibers or the hair, which do not have the drawbacks of the existing bleaching processes.

For example, one aim of the present disclosure is to provide direct dyeing systems for obtaining lightening effects, for instance, on naturally or artificially dark keratin fibers, which are resistant to successive shampooing operations, which do not damage the keratin fibers and which do not detrimentally affect their cosmetic properties.

Yet another aspect of the present disclosure is to dye keratin materials chromatically and in a manner which is persistent with respect to outside attacks. The present disclosure also provides compounds which dye keratin fibers such as the hair with a low dyeing selectivity between the root and the end, whether on natural fibers or permanent-waved fibers.

These aims can be achieved with the present disclosure, a subject of which is a process for dyeing keratin materials, for instance, keratin fibers or human keratin fibers such as the hair or further, for example, dark hair, comprising applying, to the keratin materials, a dye composition comprising, in a cosmetically acceptable medium, at least one disulfide or thiol fluorescent dye, chosen from the dyes of formulae (I) and (II) below:

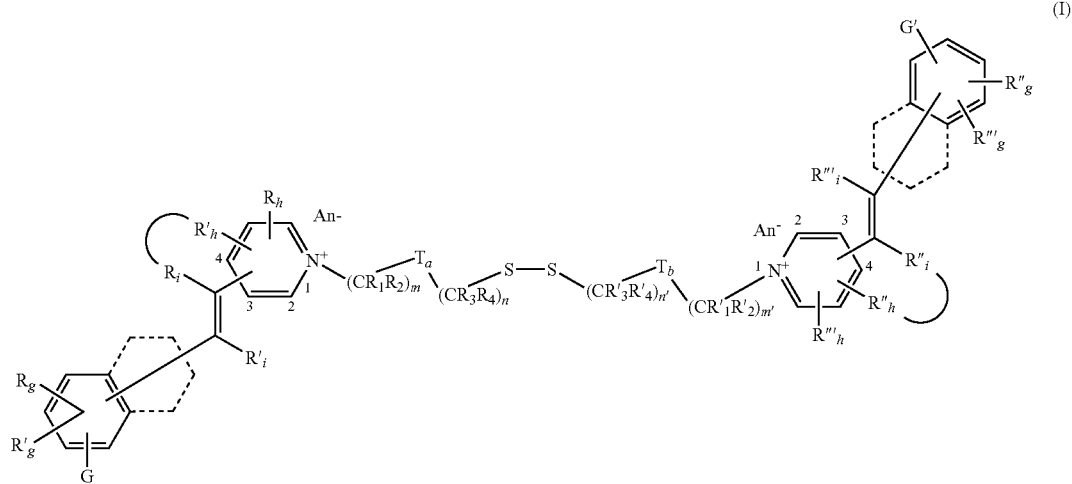

-continued

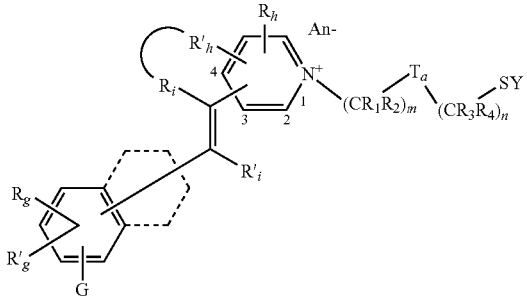

(II)

the organic or mineral acid salts thereof, optical isomers and geometric isomers thereof, or the solvates thereof, such as hydrates:

wherein:

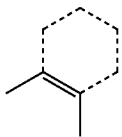

is chosen from an aryl, a heterocyclic, and a heteroaryl group fused to the phenyl ring, for instance, a benzo or indeno ring; or is absent from the phenyl ring;

G and G', which may be identical or different, are chosen from an —$NR_cR_d$ group and a ($C_1$-$C_6$)alkoxy group, which is optionally substituted or unsubstituted, or G or G' is absent;

$R_c$ and $R_d$, which may be identical or different, are chosen from a hydrogen atom, an optionally substituted ($C_1$-$C_6$) alkyl group, an aryl($C_1$-$C_4$)alkyl group, and a ($C_1$-$C_6$) alkoxy($C_1$-$C_6$)alkyl group;

$R_c$ and $R_d$ are chosen from, for instance, a hydrogen atom, a ($C_1$-$C_3$)alkyl group, and a ($C_1$-$C_3$)alkyl group substituted with i) a hydroxyl group, ii) an amino group, iii) a (di)($C_1$-$C_3$)alkylamino group, or iv) a quaternary ammonium group (R")(R''')(R'''')$N^+$—, wherein R', R", R''', and R'''', which may be identical or different, are chosen from a hydrogen atom and a ($C_1$-$C_4$)alkyl group;

or the two $R_c$ and $R_d$ radicals borne by the same nitrogen atom together form a heterocyclic or heteroaryl group; for example, the heterocycle is monocyclic and comprises between 5 and 7 members or the heteroaryl is bicyclic and comprises from 7 to 11 members; in another example, the groups are chosen from piperidinyl, imidazolyl, pyrrolidinyl, and indolyl; the heterocycle may be optionally substituted with at least one hydroxyl group;

$R_g$, $R'_g$, $R''_g$, $R'''_g$, $R_h$, and $R'''_h$, which may be identical or different, are chosen from a hydrogen atom, a halogen atom, an amino, a (di)($C_1$-$C_4$)alkylamino, a cyano, a carboxyl, a hydroxyl, a trifluoromethyl, an acylamino, a $C_1$-$C_4$ alkoxy, a $C_2$-$C_4$ (poly)hydroxyalkoxy, a ($C_1$-$C_4$) alkylcarbonyloxy ($C_1$-$C_4$)alkoxycarbonyl, a ($C_1$-$C_4$) alkylcarbonylamino, an acylamino, a carbamoyl group, a ($C_1$-$C_4$)alkylsulfonylamino group, an aminosulfonyl radical, and a ($C_1$-$C_{16}$)alkyl radical optionally substituted with a group chosen from ($C_1$-$C_{12}$)alkoxy, hydroxyl, cyano, carboxyl, amino, (di)($C_1$-$C_4$)alkylamino, and (di)($C_1$-$C_4$)alkylamino wherein the two alkyl radicals borne by the nitrogen atom of the amino group form a heterocycle comprising from 5 to 7 members and optionally comprising another heteroatom identical to or different from that of the nitrogen atom; in one example, $R_g$, $R'_g$, $R''_g$, $R'''_g$, $R_h$, and $R'''_h$ are hydrogen atoms;

or two groups $R_g$ and $R'_g$, $R''_g$ and $R'''_g$, borne by two adjacent carbon atoms, together form a benzo or indeno ring, or a fused heterocycloalkyl or fused heteroaryl group; the benzo, indeno, heterocycloalkyl, or heteroaryl ring being optionally substituted with at least one radical chosen from a halogen atom, a ($C_1$-$C_4$)alkyl, an amino, a ($C_1$-$C_4$)alkylamino, a ($C_1$-$C_4$)dialkylamino, a cyano, a carboxyl, a hydroxyl, a trifluoromethyl group, an acylamino, a $C_1$-$C_4$ alkoxy, a $C_2$-$C_4$ (poly)hydroxyalkoxy, an alkylcarbonyloxy, an alkoxycarbonyl radical, an alkylcarbonylamino radical, an acylamino, a carbamoyl radical, an alkylsulfonylamino radical, an aminosulfonyl radical, and a ($C_1$-$C_{16}$) alkyl radical optionally substituted with a group chosen from ($C_1$-$C_{12}$)alkoxy, hydroxyl, cyano, carboxyl, amino, ($C_1$-$C_4$)alkylamino, ($C_1$-$C_4$) dialkylamino, and ($C_1$-$C_4$) dialkylamino wherein the two alkyl radicals borne by the nitrogen atom of the amino group form a heterocycle comprising from 5 to 7 members and optionally comprising another heteroatom identical to or different from that of the nitrogen atom; for example, $R_g$ and $R'_g$; $R''_g$ and $R'''_g$ together form a benzo group;

or when G and/or G' are —$NR_cR_d$, two groups $R_c$ and $R'_g$, $R_d$ and $R_g$, and/or $R_c$ and $R''_g$, $R_d$ and $R'''_g$ together form a saturated heteroaryl or heterocycle, optionally substituted with at least one ($C_1$-$C_6$)alkyl group; for instance, the heterocycle or the heteroaryl comprises one or two heteroatoms chosen from nitrogen and oxygen and the heterocycle comprises between 5 and 7 members and the heteroaryl comprises between 7 and 11 members; for example, the heterocycle is chosen from morpholinyl, piperazinyl, piperidinyl, homopiperidinyl, and pyrrolidinyl groups, and the heteroaryl is an indolyl;

$R'_i$ and $R'''_i$, which may be identical or different, are chosen from a hydrogen atom and a ($C_1$-$C_4$)alkyl group; in one example, $R'_i$ and $R'''_i$ are hydrogen atoms;

$R'_h$ with $R_i$ and $R''_h$ with $R''_i$ form, together with the carbon atoms which bear them, an optionally substituted $C_5$-$C_7$ cycloalkyl group fused to the pyridinium group, such as a cyclohexyl group; it being understood that the $R'_h$ or $R''_h$ radical and the styryl group bearing the $R_i$ or $R''_i$ radical are positioned on adjacent carbon atoms of the pyridinium groups; for example, they are positioned respectively on carbon atoms 3 and 4 of the pyridinium groups;

$R_1, R_2, R_3, R_4, R'_1, R'_2, R'_3,$ and $R'_4$, which may be identical or different, are chosen from:
- a hydrogen atom,
- a $(C_1-C_4)$alkyl group,
- a $(C_1-C_{12})$alkoxy,
- a hydroxyl,
- a cyano,
- a $—C(O)O^-M^+$, wherein $M^+$ is an alkali metal or $M^+$ and $An^-$ are absent,
- a carboxyl,
- a (di)$(C_1-C_4)$(alkyl)amino, said alkyl radicals optionally form, with the nitrogen atom which bears them, a heterocycle comprising from 5 to 7 members, optionally comprising another heteroatom which may or may not be different from nitrogen; for instance, $R_1$, $R_2, R_3, R_4, R'_1, R'_2, R'_3,$ and $R'_4$ are hydrogen atoms or a $—C(O)O^-M^+$ group; in another embodiment, $R_1$, $R_2, R_3, R_4, R'_1, R'_2, R'_3,$ and $R'_4$ are hydrogen atoms;

$T_a$ and $T_b$, which may be identical or different, are chosen from:
- i) a σ covalent bond;
- ii) at least one radical or combination thereof, chosen from $—SO_2—$, $—O—$, $—S—$, $—N(R)—$, $—N^+(R)(R^o)—$, and $—C(O)—$, wherein R and $R^o$, which may be identical or different, are chosen from a hydrogen atom, a $C_1-C_4$ alkyl radical, a $C_1-C_4$ hydroxyalkyl radical, and an aryl$(C_1-C_4)$alkyl; in one embodiment, $T_a$ is identical to $T_b$ and they are a σ covalent bond or a group chosen from $—N(R)—$, $—C(O)—$, $—C(O)—N(R)—$, $—N(R)—C(O)—$, $—C(O)—N(R)—C(O)—$, $—O—C(O)—$, $—C(O)—O—$, and $—N^+(R)(R^o)—$, wherein R and $R^o$, which may be identical or different, are chosen from a hydrogen atom and a $C_1-C_4$ alkyl group; in yet another embodiment, $T_a$ and $T_b$ are chosen from $—C(O)—N(R)—$ and $—N(R)—C(O)—$; and
- (iii) a monocyclic, cationic or noncationic, heterocycloalkyl or heteroaryl radical, for example, comprising two heteroatoms such as two nitrogen atoms, and comprising from 5 to 7 members, such as imidazolium, pyridinium, or pyrrolidinium optionally substituted with a $(C_1-C_4)$ alkyl group, such as methyl;

m, m', n, and n', which may be identical or different, are chosen from integers ranging from 0 to 6, wherein m+n and m'+n', which may be identical or different, are chosen from integers ranging from 1 to 10; for example, the sum m+n is equal to m'+n' and is an integer ranging from 2 to 4, such as, m+n=m'+n'=2;

$An^-$ is an anionic counterion; and

Y is chosen from:
- i) a hydrogen atom;
- ii) an alkali metal;
- iii) an alkaline earth metal;
- iv) an ammonium group: $N^+R^\alpha R^\beta R^\gamma R^\delta$ and a phosphonium group: $P^+R^\alpha R^\beta R^\gamma R^\delta$ wherein $R^\alpha$, $R^\beta$, $R^\gamma$, and $R^\delta$, which may be identical or different, are chosen from a hydrogen atom and a $(C_1-C_4)$alkyl group; and
- v) a thiol-function-protecting group;

wherein, when the compound of formula (I) or (II) comprises other cationic parts, it is associated with one or more anionic counterions allowing formula (I) or (II) to achieve electroneutrality.

Another aspect of the present disclosure is a dye composition comprising, in a cosmetically acceptable medium, at least one disulfide fluorescent dye of formula (I) or one thiol fluorescent dye of formula (II) as disclosed herein, and optionally a reducing agent.

Another aspect of the present disclosure is at least one disulfide fluorescent dye of formula (I) and at least one thiol fluorescent dye of formula (II).

The dyeing process according to the present disclosure may be used to visibly color dark keratin materials, for instance, dark human keratin fibers such as dark hair.

Furthermore, the process of the present disclosure may be used to obtain a coloring of keratin materials, for example, human keratin fibers such as the hair, without damaging said material, which is persistent with respect to shampooing operations, common attacks (for example, sunlight and perspiration) and other hair treatments. The process of the present disclosure also may be used to obtain lightening of keratin materials such as keratin fibers, for instance, dark keratin fibers such as dark hair.

The dyes of the present disclosure are, moreover, stable with respect to oxidants, and have a satisfactory solubility in cosmetic dyeing media. These dyes extend the color range to yellows and oranges. After application to keratin fibers, the dyes of formula (I) or (II) dye the keratin materials chromatically and in a manner which is persistent with respect to outside attacks, and with low dyeing selectivity between the root and the end, and on various types of fibers.

BRIEF DESCTIPTION OF FIG. 1

FIG. 1 shows the curves of reflectance of TH4 locks treated with dyes 1 and 2.

As used herein, "dark keratin material" means keratin material that exhibits a lightness L* measured in the C.I.E. L*a*b* system of less than or equal to 45, for example, less than or equal to 40, given that, moreover, L*=0 is equivalent to black and L*=100 is equivalent to white.

As used herein, "naturally or artificially dark hair" means hair whose tone height is less than or equal to 6 (dark blond), for instance, less than or equal to 4 (chestnut-brown).

The lightening of the hair is evaluated by the variation in "tone height" before and after application of the compound of formula (I) or (II). It is understood that the notion of "tone" is based on the classification of the natural shades, one tone separating each shade from the shade immediately following or preceding it. This definition and the classification of the natural shades are well known to hair styling professionals and are published in the book "Science des traitements capillaires" [Hair Treatment Sciences], by Charles Zviak 1988, published by Masson, pp. 215 and 278.

The tone heights range from 1 (black) to 10 (very light blond), one unit corresponding to one tone; the higher the figure, the lighter the shade.

An artificially colored hair is a hair whose color has been modified by a dyeing treatment, for example dyeing with direct dyes or oxidation dyes.

As used herein, "bleached hair" means hair whose tone height is greater than 4 (chestnut-brown), for example, greater than 6 (dark blond).

One means for measuring the lightening effect given to the hair after application of the fluorescent dyes of the present disclosure is to use the phenomenon of hair reflectance.

The composition disclosed herein should, after application to dark hair, lead to at least one of the results below:

Interest is focused on the hair reflectance performance levels when said hair is irradiated with visible light in the wavelength range from 400 to 700 nanometers.

The curves of reflectance as a function of wavelength, of the hair treated with the composition of the present disclosure and of untreated hair, are then compared.

The curve corresponding to the treated hair should show a reflectance in the wavelength range of from 500 to 700 nanometers which is higher than the curve corresponding to the untreated hair.

This means that, in the wavelength range of from 540 to 700 nanometers, there is at least one range where the reflectance curve corresponding to the treated hair is higher than the reflectance curve corresponding to the untreated hair. As used herein, "higher" means a difference of at least 0.05% in reflectance, for example, at least 0.1%. All the same, there may be, in the wavelength range of from 540 to 700 nanometers, at least one range where the reflectance curve corresponding to the treated hair is superimposable on or lower than the reflectance curve corresponding to the untreated hair.

For example, the wavelength where the difference is at a maximum between the reflectance curve of the treated hair and that of the untreated hair is within the wavelength range of from 500 to 650 nanometers, for instance, within the wavelength range of from 550 to 620 nanometers.

For the purpose of the present disclosure, and unless otherwise indicated, the "aryl" or "heteroaryl" radicals, or the aryl or heteroaryl part of a radical, may be substituted with at least one substituent borne by a carbon atom, chosen from:

a $C_1$-$C_{16}$, such as $C_1$-$C_8$, an alkyl radical optionally substituted with at least one radical chosen from the radicals: hydroxyl, $C_1$-$C_2$ alkoxy, $C_2$-$C_4$(poly)hydroxyalkoxy, acylamino, and amino substituted with two $C_1$-$C_4$ alkyl radicals, which may be identical or different, optionally bearing at least one hydroxyl group, or the two radicals optionally forming, with the nitrogen atom to which they are attached, a heterocycle comprising from 5 to 7 members, such as 5 or 6 members, which is saturated or unsaturated, which is optionally substituted, and which optionally comprises another heteroatom which may be identical or different from the nitrogen;

a halogen atom such as chlorine, fluorine, or bromine;

a hydroxyl group;

a $C_1$-$C_2$ alkoxy radical;

$C_1$-$C_2$ alkylthio radical;

a $C_2$-$C_4$ (poly)hydroxyalkoxy radical;

an amino radical;

a 5- or 6-membered heterocycloalkyl radical;

an optionally cationic 5- or 6-membered heteroaryl radical, such as imidazolium, optionally substituted with a $C_1$-$C_4$ alkyl radical, such as methyl;

an amino radical substituted with one or two $C_1$-$C_6$ alkyl radicals, which may be identical or different, optionally bearing at least:
  i) one hydroxyl group, and/or
  ii) one amino group optionally substituted with one or two optionally substituted $C_1$-$C_3$ alkyl radicals, said alkyl radicals optionally forming, with the nitrogen atom to which they are attached, a heterocycle comprising from 5 to 7 members, which is saturated or unsaturated, which is optionally substituted, and which optionally comprises at least one other heteroatom which may or may not be different from nitrogen;

—NR—COR' wherein the R radical is chosen from a hydrogen atom and a $C_1$-$C_4$ alkyl radical optionally bearing at least one hydroxyl group, and the R' radical is chosen from a $C_1$-$C_2$ alkyl radical;

(R)$_2$N—CO— wherein the R radicals, which may or may not be identical, are chosen from a hydrogen atom and a $C_1$-$C_4$ alkyl radical optionally bearing at least one hydroxyl group;

R'SO$_2$—NR— wherein the R radical is chosen from a hydrogen atom and a $C_1$-$C_4$ alkyl radical optionally bearing at least one hydroxyl group, and the R' radical is chosen from a $C_1$-$C_4$ alkyl radical and a phenyl radical;

(R)$_2$N—SO$_2$— wherein the R radicals, which may or may not be identical, are chosen from a hydrogen atom and a $C_1$-$C_4$ alkyl radical optionally bearing at least one hydroxyl group;

a carboxylic radical in acid or salified form, for instance, with an alkali metal or an ammonium, which is substituted or unsubstituted;

a cyano group; and a polyhaloalkyl group comprising from 1 to 6 carbon atoms and from 1 to 6 halogen atoms, which may be identical or different; the polyhaloalkyl group can be, for example, trifluoromethyl.

For the purpose of the present disclosure, and unless otherwise indicated, the cyclic or heterocyclic part of a nonaromatic radical may be substituted with at least one substituent, chosen from the groups:

hydroxyl;

$C_1$-$C_4$ alkoxy;

$C_1$-$C_4$ alkyl;

$C_2$-$C_4$ (poly)hydroxyalkoxy;

a $C_1$-$C_2$ alkylthio radical;

RCO—NR'— wherein the R' radical is chosen from a hydrogen atom and a $C_1$-$C_4$ alkyl radical optionally bearing at least one hydroxyl group, and the R radical is chosen from a $C_1$-$C_2$ alkyl radical and an amino radical substituted with two $C_1$-$C_4$ alkyl groups, which may be identical or different, optionally bearing at least one hydroxyl group;

RCO—O— wherein the R radical is chosen from a $C_1$-$C_4$ alkyl radical and an amino radical substituted with one or two $C_1$-$C_4$ alkyl groups, which may be identical or different, optionally bearing at least one hydroxyl group, said alkyl radicals possibly forming, with the nitrogen atom to which they are attached, a heterocycle comprising from 5 to 7 members, which is saturated or unsaturated, which is optionally substituted, and which optionally comprises at least one other heteroatom which may or may not be different from nitrogen; and RO—CO— wherein the R radical is chosen from a $C_1$-$C_4$ alkyl radical optionally bearing at least one hydroxyl group.

For the purpose of the present disclosure, and unless otherwise indicated, a cyclic or heterocyclic radical or a nonaromatic part of an aryl or heteroaryl radical optionally substituted with at least one oxo or thioxo groups.

For the purpose of the present disclosure, and unless otherwise indicated, an "aryl" radical comprises a condensed or noncondensed, monocyclic or polycyclic group comprising from 6 to 22 carbon atoms, and at least one ring of which is aromatic; for instance, the aryl radical is a phenyl, biphenyl, naphthyl, indenyl, anthracenyl, or tetrahydronaphthyl.

For the purpose of the present disclosure, and unless otherwise indicated, a "diarylalkyl" radical comprises a group comprising, on the same carbon atom of an alkyl group, two aryl groups, which may be identical or different, such as diphenylmethyl or 1,1-diphenylethyl.

For the purpose of the present disclosure, and unless otherwise indicated, a "heteroaryl radical" comprises an optionally cationic, condensed or noncondensed, monocyclic or polycyclic group comprising from 5 to 22 members and from 1 to 6 heteroatoms chosen from a nitrogen, oxygen, sulfur, and selenium atom, and at least one ring of which is aromatic; by way of non-limiting example, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenooxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl and its ammonium salt.

For the purpose of the present disclosure, and unless otherwise indicated, a "diheteroarylalkyl" radical comprises a group comprising, on the same carbon atom of an alkyl group, two heteroaryl groups, which may be identical or different, such as difurylmethyl, 1,1-difurylethyl, dipyrrolylmethyl, or dithienylmethyl.

For the purpose of the present disclosure, and unless otherwise indicated, a "cyclic radical" comprises a condensed or noncondensed, monocyclic or polycyclic, nonaromatic cycloalkyl radical comprising from 5 to 22 carbon atoms, optionally comprising one or more unsaturations; for example, the cyclic radical is a cyclohexyl.

For the purpose of the present disclosure, and unless otherwise indicated, a "sterically hindered cyclic" radical comprises a substituted or unsubstituted, aromatic or nonaromatic, cyclic radical hindered by steric effect or constraint, comprising from 6 to 14 members, which may be bridged; by way of sterically hindered radicals, non-limiting mention may be made of bicyclo[1.1.0]butane, mesityls such as 1,3,5-trimethylphenyl, 1,3,5-tri-tert-butylphenyl, 1,3,5-isobutylphenyl, 1,3,5-trimethylsilylphenyl, and adamantyl.

For the purpose of the present disclosure, and unless otherwise indicated, a "heterocyclic radical or heterocycle" comprises a condensed or noncondensed, monocyclic or polycyclic, nonaromatic radical comprising from 5 to 22 members, comprising from 1 to 6 heteroatoms chosen from nitrogen, oxygen, sulfur, and selenium.

For the purpose of the present disclosure, and unless otherwise indicated, an "alkyl radical" comprises a linear or branched, $C_1$-$C_{16}$, such as $C_1$-$C_8$, hydrocarbon-based radical.

For the purpose of the present disclosure, and unless otherwise indicated, "optionally substituted" assigned to the alkyl radical means that said alkyl radical may be substituted with at least one radical chosen from the radicals: i) hydroxyl; ii) $C_1$-$C_4$ alkoxy; iii) acylamino; iv) amino optionally substituted with one or two $C_1$-$C_4$ alkyl radicals, which may be identical or different, said alkyl radicals possibly forming, with the nitrogen atom which bears them, a heterocycle comprising from 5 to 7 members, optionally comprising another heteroatom which may or may not be different from nitrogen; v) or a quaternary ammonium group —N$^+$R'R''R''', M$^-$ for which R', R'', R''', which may be identical or different, are chosen from a hydrogen atom and a $C_1$-$C_4$ alkyl group, or —N$^+$R'R''R''' forms a heteroaryl such as imidazolium optionally substituted with a $C_1$-$C_4$ alkyl group, and M$^-$ is chosen from the counterion of the corresponding organic acid, mineral acid, and halide.

For the purpose of the present disclosure and unless otherwise indicated, an "alkoxy radical" comprises an alkyloxy or alkyl-O-radical for which the alkyl radical is a linear or branched, $C_1$-$C_{16}$ hydrocarbon-based radical, for instance, a $C_1$-$C_8$ hydrocarbon-based radical.

For the purpose of the present disclosure, and unless otherwise indicated, an "alkylthio radical" comprises an alkyl-S— radical for which the alkyl radical is a linear or branched, $C_1$-$C_{16}$ hydrocarbon-based radical, such as a $C_1$-$C_8$ hydrocarbon-based radical. When the alkylthio group is optionally substituted, this means that the alkyl group is optionally substituted as defined above.

For the purpose of the present disclosure, and unless otherwise indicated, an "organic or mineral acid salt", for instance, is chosen from a salt derived: i) from hydrochloric acid HCl; ii) from hydrobromic acid HBr; iii) from sulfuric acid $H_2SO_4$; iv) from alkylsulfonic acids: Alk-S(O)$_2$OH such as methylsulfonic acid and ethylsulfonic acid; v) from arylsulfonic acids: Ar—S(O)$_2$OH such as from benzenesulfonic acid and from toluenesulfonic acid; vi) from citric acid; vii) from succinic acid; viii) from tartaric acid; ix) from lactic acid; x) from alkoxysulfinic acids: Alk-O—S(O)OH such as from methoxysulfinic acid and from ethoxysulfinic acid; xi) from aryloxysulfinic acids such as from tolueneoxysulfinic acid and from phenoxysulfinic acid; xii) from phosphoric acid $H_3PO_4$; xiii) from acetic acid $CH_3COOH$; xiv) from triflic acid $CF_3SO_3H$; and xv) from tetrafluoroboric acid $HBF_4$.

For the purpose of the present disclosure, and unless otherwise indicated, an "anionic counterion" is an anion or an anionic group associated with the cationic charge of the dye; as non-limiting examples, the anionic counterion is chosen from: i) halides such as chloride or bromide; ii) nitrates; iii) sulfonates, among which are $C_1$-$C_6$ alkyl sulfonates: Alk-S(O)$_2$O$^-$ such as methyl sulfonate or mesylate and ethyl sulfonate; iv) aryl sulfonates: Ar—S(O)$_2$O$^-$ such as benzene sulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) arylsulfates: Ar—O—S(O)O$^-$ such as benzenesulfate and toluenesulfate; xi) alkoxysulfates: Alk-O—S(O)$_2$O$^-$ such as methoxy sulfate and ethoxy sulfate; xii) aryloxysulfates: Ar—O—S(O)$_2$O$^-$; xiii) phosphate; xiv) acetate; xv) triflate; and xvi) borates such as tetrafluoroborate.

For the purpose of the present disclosure, and unless otherwise indicated, the "solvates" comprise the hydrates or the association with linear or branched $C_1$-$C_4$ alcohols such as ethanol, isopropanol, or n-propanol.

The disulfide fluorescent dyes of formula (I) or thiol fluorescent dyes of formula (II) are compounds capable of absorbing in the UV radiation or visible range at a wavelength $\gamma_{abs}$ ranging from 250 to 800 nm and capable of re-emitting in the visible range at an emission wavelength $\gamma_{em}$ ranging from 400 to 800 nm.

For example, the fluorescent compounds of formula (I) or (II) of the present disclosure are dyes capable of absorbing in the visible range $\gamma_{abs}$ ranging from 400 and 800 nm and of re-emitting in the visible range $\gamma_{em}$ ranging from 400 and 800 nm. In another embodiment, the dyes of formula (I) or (II) are dyes capable of absorbing at a $\gamma_{abs}$ ranging from 420 and 550 nm and of re-emitting in the visible range at a $\gamma_{em}$ ranging from 470 and 600 nm.

The fluorescent compounds of the present disclosure of formula (II) comprise an SY function which may be in the covalent form —S—Y or ionic form —S$^-$Y$^+$ depending on the nature of Y and on the pH of the medium.

In another embodiment, the thiol fluorescent dyes of formula (II) comprise an SY function where Y is chosen from a hydrogen atom and an alkali metal. For example, Y is a hydrogen atom.

In another embodiment of the present disclosure, in the abovementioned formula (II), Y is a protecting group known to those skilled in the art, for instance those described in the books "*Protective Groups in Organic Synthesis*", T. W. Greene, John Wiley & Sons Ed., NY, 1981, pp. 193-217; "*Protecting Groups*", P. Kocienski, Thieme, 3rd Ed., 2005, Chap. 5. It being understood that Y as a protective group cannot constitute with the sulphur atom on which it is linked a disulfide dye, i.e., it cannot constitute a formula (I). Y as the protective group cannot be a group directly linked to the sulphur atom of formula (II) via another non oxidized sulphur atom.

By way of non-limiting example, when Y is a thiol-function-protecting group, Y may be chosen from the following radicals:

$(C_1-C_4)$alkylcarbonyl;
$(C_1-C_4)$alkylthiocarbonyl;
$(C_1-C_4)$alkoxycarbonyl;
$(C_1-C_4)$alkoxythiocarbonyl;
$(C_1-C_4)$alkylthiothiocarbonyl;
(di)$(C_1-C_4)$(alkyl)aminocarbonyl;
(di)$(C_1-C_4)$(alkyl)aminothiocarbonyl;
arylcarbonyl such as phenylcarbonyl;
aryloxycarbonyl;
aryl$(C_1-C_4)$alkoxycarbonyl;
(di)$(C_1-C_4)$(alkyl)aminocarbonyl such as dimethylaminocarbonyl;
$(C_1-C_4)$(alkyl)arylaminocarbonyl;
$SO_3^-$, $M^+$ wherein $M^+$ is chosen from an alkali metal such as sodium or potassium, or $An^-$ of formula (II) is absent and $M^+$ is also absent;
optionally substituted aryl such as phenyl, dibenzosuberyl, or 1,3,5-cycloheptatrienyl,
optionally substituted heteroaryl; as non-limiting examples, the cationic or noncationic heteroaryl comprising from 1 to 4 heteroatoms below:
  i) monocyclic comprising 5, 6, or 7 members, such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium,
  ii) bicyclic comprising 8 to 11 members, such as indolyl, indolinium, benzoimidazolyl, benzoimidazolium, benzoxazolyl, benzoxazolium, dihydrobenzoxazolinyl, benzothiazolyl, benzothiazolium, pyridoimidazolyl, pyridoimidazolium, thienocycloheptadienyl, these monocyclic or bicyclic groups being optionally substituted with at least one group such as $(C_1-C_4)$ alkyl, for instance methyl, or polyhalo$(C_1-C_4)$alkyl, for instance trifluoromethyl;
  iii) or tricyclic ABC below:

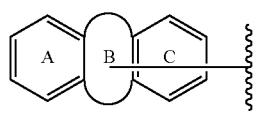

wherein the two rings A and C optionally comprise a heteroatom, and the ring B comprises a 5-, 6-, or 7-membered, such as a 6-membered ring and comprise at least one heteroatom, for instance piperidyl or pyranyl;
optionally cationic, optionally substituted heterocycloalkyl, the heterocycloalkyl group chosen from, for example, a saturated or partially saturated, 5-, 6-, or 7-membered monocyclic group comprising from 1 to 4 heteroatoms chosen from oxygen, sulfur, and nitrogen, such as di/tetrahydrofuranyl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidinyl, morpholinyl, di/tetra/hexahydroazepinyl, and di/tetrahydropyrimidinyl, these groups being optionally substituted with at least one group chosen from, for example, $(C_1-C_4)$ alkyl, oxo, and thioxo; or the heterocycle is the following group:

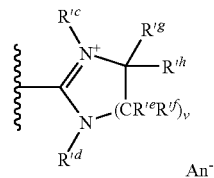

wherein $R^{\prime c}$, $R^{\prime d}$, $R^{\prime e}$, $R^{\prime f}$, $R^{\prime g}$, and $R^{\prime h}$, which may be identical or different, are chosen from hydrogen atoms and $(C_1-C_4)$ alkyl groups; or two groups $R^{\prime g}$ with $R^{\prime h}$, and/or $R^{\prime e}$ with $R^{\prime f}$, form an oxo or thioxo group; or $R^{\prime g}$ with $R^{\prime e}$ together form a cycloalkyl; and v is an integer ranging from 1 to 3; for instance, $R^{\prime c}$ to $R^{\prime h}$ are hydrogen atoms; and $An^{\prime -}$ is a counterion;
isothiouronium;
—$C(NR^{\prime c}R^{\prime d})$=$N^+R^{\prime e}R^{\prime f}$; $An^-$, wherein $R^{\prime c}$, $R^{\prime d}$, $R^{\prime e}$, and $R^{\prime f}$, which may be identical or different, are chosen from hydrogen atoms and $(C_1-C_4)$alkyl groups; for example, $R^{\prime c}$ to $R^{\prime f}$ are hydrogen atoms; and $An^{\prime -}$ is a counterion;
isothiourea;
—$C(NR^{\prime c}R^{\prime d})$=$NR^{\prime e}$; $An^-$, wherein $R^{\prime c}$, $R^{\prime d}$, $R^{\prime e}$, and $An^-$ are as defined above;
optionally substituted (di)aryl$(C_1-C_4)$alkyl, such as 9-anthracenylmethyl, phenylmethyl, or diphenylmethyl optionally substituted with at least one group chosen from $(C_1-C_4)$ alkyl, $(C_1-C_4)$ alkoxy such as methoxy, hydroxyl, alkylcarbonyl, and (di)$(C_1-C_4)$(alkyl)amino such as dimethylamino;
optionally substituted (di)heteroaryl$(C_1-C_4)$alkyl, the heteroaryl group is, for instance, cationic or noncationic, and monocyclic, comprising 5 or 6 members and from 1 to 4 heteroatoms chosen from nitrogen, oxygen, and sulfur, such as the groups pyrrolyl, furanyl, thiophenyl, pyridyl, pyridyl N-oxide such as 4-pyridyl or 2-pyridyl N-oxide, pyrylium, pyridinium, or triazinyl, optionally substituted with one or more groups such as alkyl, for instance methyl, in one embodiment, the (di)heteroaryl $(C_1-C_4)$alkyl is (di)heteroarylmethyl or (di)heteroarylethyl;
$CR^1R^2R^3$ with $R^1$, $R^2$, and $R^3$, which may be identical or different, are chosen from a halogen atom or a group chosen from:
  i) $(C_1-C_4)$alkyl;
  ii) $(C_1-C_4)$alkoxy;
  iii) optionally substituted aryl, such as phenyl optionally substituted with at least one group such as $(C_1-C_4)$ alkyl, $(C_1-C_4)$alkoxy, or hydroxyl;

iv) optionally substituted heteroaryl, such as thiophenyl, furanyl, pyrrolyl, pyranyl, or pyridyl, optionally substituted with a $(C_1$-$C_4)$alkyl group; and v) $P(Z^1)R'^1R'^2R'^3$, wherein $R'^1$ and $R'^2$, which may be identical or different, are chosen from hydroxyl, $(C_1$-$C_4)$alkoxy, and alkyl groups, $R'^3$ is chosen from a hydroxyl and a $(C_1$-$C_4)$alkoxy group, and $Z^1$ is chosen from an oxygen atom and sulfur atom;

a sterically hindered cyclic; and optionally substituted alkoxyalkyl, such as methoxymethyl (MOM), ethoxyethyl (EOM), or isobutoxymethyl.

According to another embodiment, the protected thiol fluorescent dyes of formula (II) comprising a group Y is chosen from: i) a cationic, aromatic 5- or 6-membered monocyclic heteroaryl group comprising from 1 to 4 heteroatoms chosen from oxygen, sulfur, and nitrogen, non-limiting examples include oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinyl, pyrazinium, pyridazinium, triazinium, tetrazinium, oxazepinium, thiepinyl, thiepinium, and imidazolium; ii) a cationic 8- to 11-membered bicyclic heteroaryl group, such as indolinium, benzoimidazolium, benzoxazolium or benzothiazolium, these monocyclic or bicyclic heteroaryl groups being optionally substituted with at least one group such as alkyl, for instance methyl, or polyhalo$(C_1$-$C_4)$alkyl, for instance trifluoromethyl; iii) a heterocyclic group below:

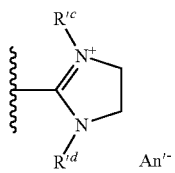

wherein $R'^c$ and $R'^d$, which may be identical or different, are chosen from a hydrogen atom and a $(C_1$-$C_4)$alkyl group; for instance, $R'^c$ and $R'^d$ are chosen from a $(C_1$-$C_4)$alkyl group such as methyl; and $An'^-$ is an anionic counterion.

In at least one embodiment, Y is a group chosen from oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinium, pyridazinium, triazinium and imidazolium, benzoimidazolium, benzoxazolium, benzothiazolium, these groups being optionally substituted with at least one $(C_1$-$C_4)$alkyl group, such as methyl.

In another embodiment, Y is an alkali metal or a protecting group such as:

$(C_1$-$C_4)$alkylcarbonyl, such as methylcarbonyl or ethylcarbonyl;

arylcarbonyl such as phenylcarbonyl;

$(C_1$-$C_4)$alkoxycarbonyl;

aryloxycarbonyl;

aryl$(C_1$-$C_4)$alkoxycarbonyl;

(di)$(C_1$-$C_4)$(alkyl)aminocarbonyl, such as dimethylaminocarbonyl;

$(C_1$-$C_4)$(alkyl)arylaminocarbonyl;

optionally substituted aryl, such as phenyl;

5- or 6-membered monocyclic heteroaryl, such as imidazolyl or pyridyl;

5- or 6-membered cationic monocyclic heteroaryl, such as pyrylium, pyridinium, pyrimidinium, pyrazinium, pyridazinium, triazinium, or imidazolium; these groups being optionally substituted with at least one identical or different $(C_1$-$C_4)$alkyl group, such as methyl;

8- to 11-membered cationic bicyclic heteroaryl, such as benzoimidazolium or benzoxazolium; these groups being optionally substituted with at least one identical or different $(C_1$-$C_4)$alkyl group, such as methyl;

cationic heterocycle of the following formula:

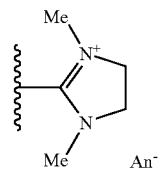

isothiouronium —$C(NH_2)$=$N^+H_2$; $An^-$;

isothiourea —$C(NH_2)$=NH;

$SO_3^-$, $M^+$, wherein $M^+$ comprises an alkali metal such as sodium or potassium, or when $An^-$ of formula (II) is absent and $M^+$ is also absent.

In at least one embodiment of the present disclosure, the disulfide fluorescent dyes of formula (I) have a C2 axis of symmetry between the two sulfur atoms of the central disulfide radical.

In another embodiment, the dyes of the present disclosure are chosen from one of the two formulae (Ia) and (IIa) which have a phenyl group bearing the amino group $R_cR_dN$—, for instance in the para-position, i.e., in the 1-4-position, with respect to the styryl group:

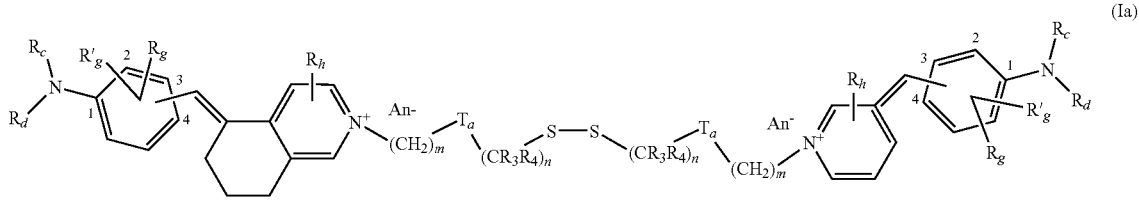

(Ia)

(IIa)

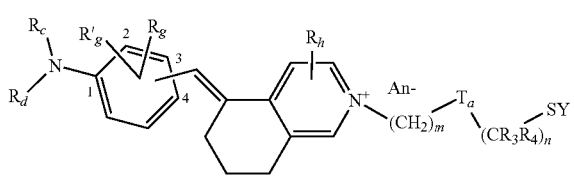

wherein:
R$_3$ and R$_4$, which may be identical or different, are chosen from:
  a hydrogen atom,
  a (C$_1$-C$_4$)alkyl group,
  —C(O)O$^-$M$^+$, wherein M$^+$ comprises an alkali metal or M$^+$ is absent and An$^-$ is also absent,
  carboxyl;
R$_g$, R'$_g$, and R$_h$, which may be identical or different, are chosen from a hydrogen atom, a halogen atom, a (di)(C$_1$-C$_4$)(alkyl)amino, a hydroxyl, an acylamino, a (C$_1$-C$_4$)alkoxy group, a (C$_1$-C$_4$)alkylcarbonylamino group, and a (C$_1$-C$_6$)alkyl radical; for example, R$_g$, R'$_g$, and R$_h$ are hydrogen atoms;
two groups R$_c$, and R'$_g$ and/or R$_d$ and R$_g$ together form a saturated heterocycle or a heteroaryl, optionally substituted with at least one (C$_1$-C$_6$)alkyl group, for instance, a heterocycle and the heteroaryl comprising one or two heteroatoms chosen from nitrogen and oxygen, the heterocycle comprising between 5 and 7 members and the heteroaryl comprising between 7 and 11 members; in another example, the heterocycle is chosen from morpholinyl, piperazinyl, piperidinyl, and pyrrolidinyl groups, and the heteroaryl is an indolyl;
R$_c$ and R$_d$, which may be identical or different, are chosen from a hydrogen atom, an optionally substituted (C$_1$-C$_6$) alkyl group, and an aryl(C$_1$-C$_4$)alkyl group; for example, R$_c$ and R$_d$ are a (C$_1$-C$_4$)alkyl group optionally substituted with i) a hydroxyl group, ii) an amino group, iii) a (di)(C$_1$-C$_3$)alkylamino group, or iv) a quaternary ammonium group (R'')(R''')(R'''')N$^+$—, wherein R', R'', R''' and R'''', which may be identical or different, are chosen from a hydrogen atom and a (C$_1$-C$_4$)alkyl group; for instance, the alkyl group is substituted with a hydroxyl group;
or the two radicals R$_c$ and R$_d$ borne by the same nitrogen atom together form a heterocyclic or heteroaryl group; for example, the heterocycle is monocyclic and comprises between 5 and 7 members and is optionally substituted with, for instance, one or two hydroxyl and/or (C$_1$-C$_4$)alkyl groups, which may be identical or different; for example, the groups are chosen from piperidino and pyrrolidino; said heterocyclic group being substituted, for instance, with 1 or 2 hydroxyl substituents;
T$_a$ is chosen from a σ covalent bond and a group chosen from: —N(R)—, —C(O)—N(R)—, and N(R)—C(O)—; for instance, —C(O)—N(R)—, —N(R)—C(O)—, wherein R is chosen from a hydrogen atom, a (C$_1$-C$_4$)alkyl group, a hydroxy(C$_1$-C$_4$)alkyl group, and an aryl(C$_1$-C$_4$)alkyl group, or a covalent bond;
m and n, which may be identical or different, are chosen from integers ranging from 1 to 6, wherein the sum m+n is an integer ranging from 2 to 6; for example, m is 1 and/or n is an integer ranging from 1 to 3;
An$^-$ is an anionic counterion; and
Y is as defined above;
it being understood that, when the compounds of formula (Ia) or (IIa) contain other cationic parts, they are associated with one or more anionic counterions which allow formula (Ia) or (IIa) to achieve electroneutrality.

By way of non-limiting example, mention may be made of the fluorescent dyes corresponding to formulae (II):

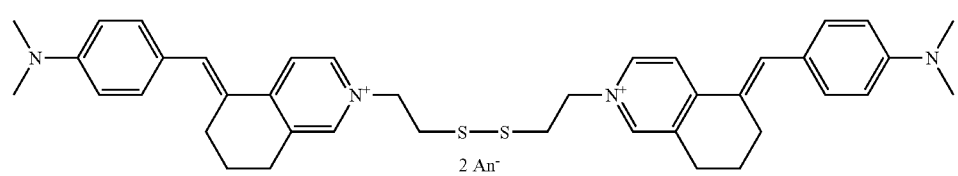

1

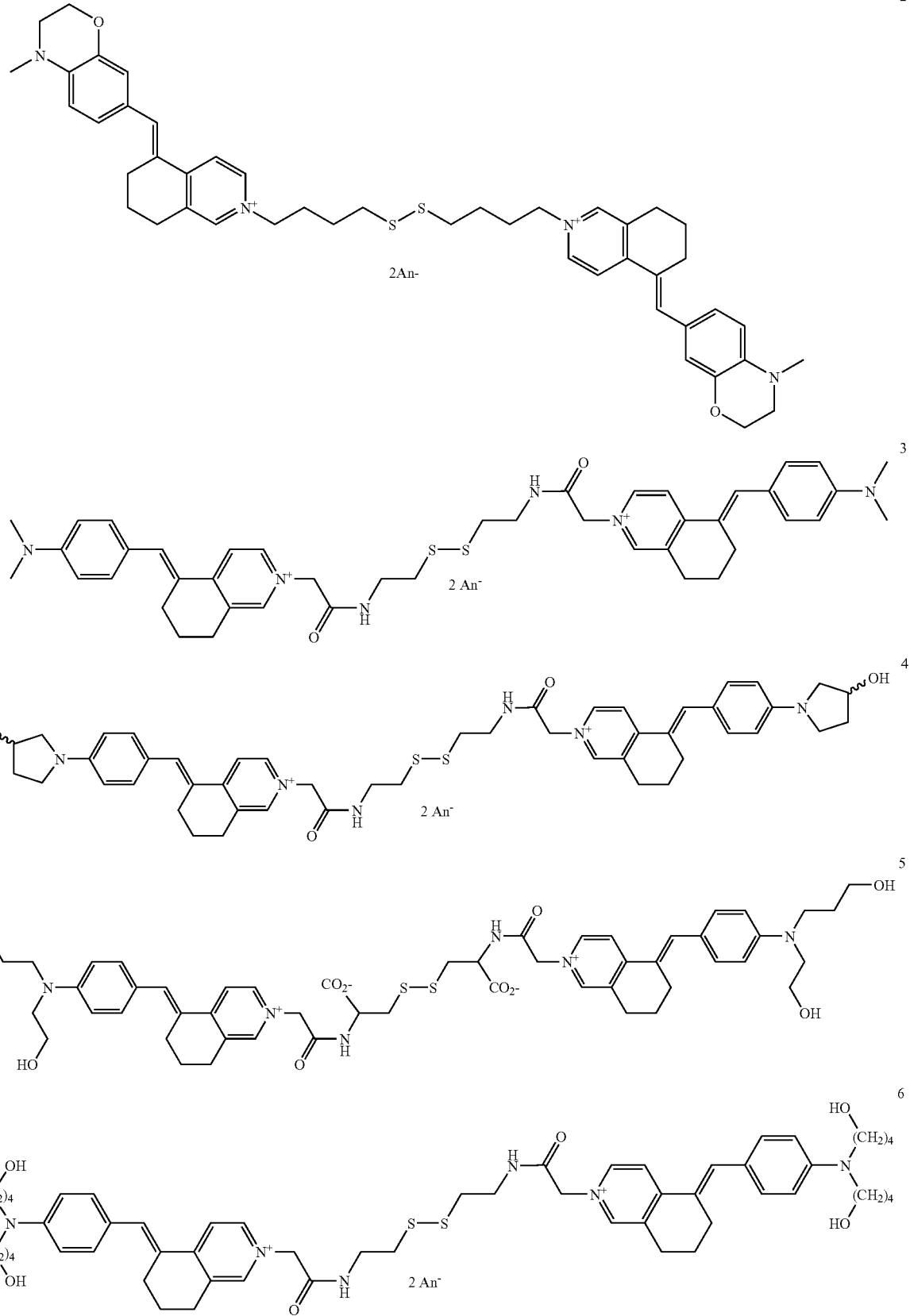

-continued
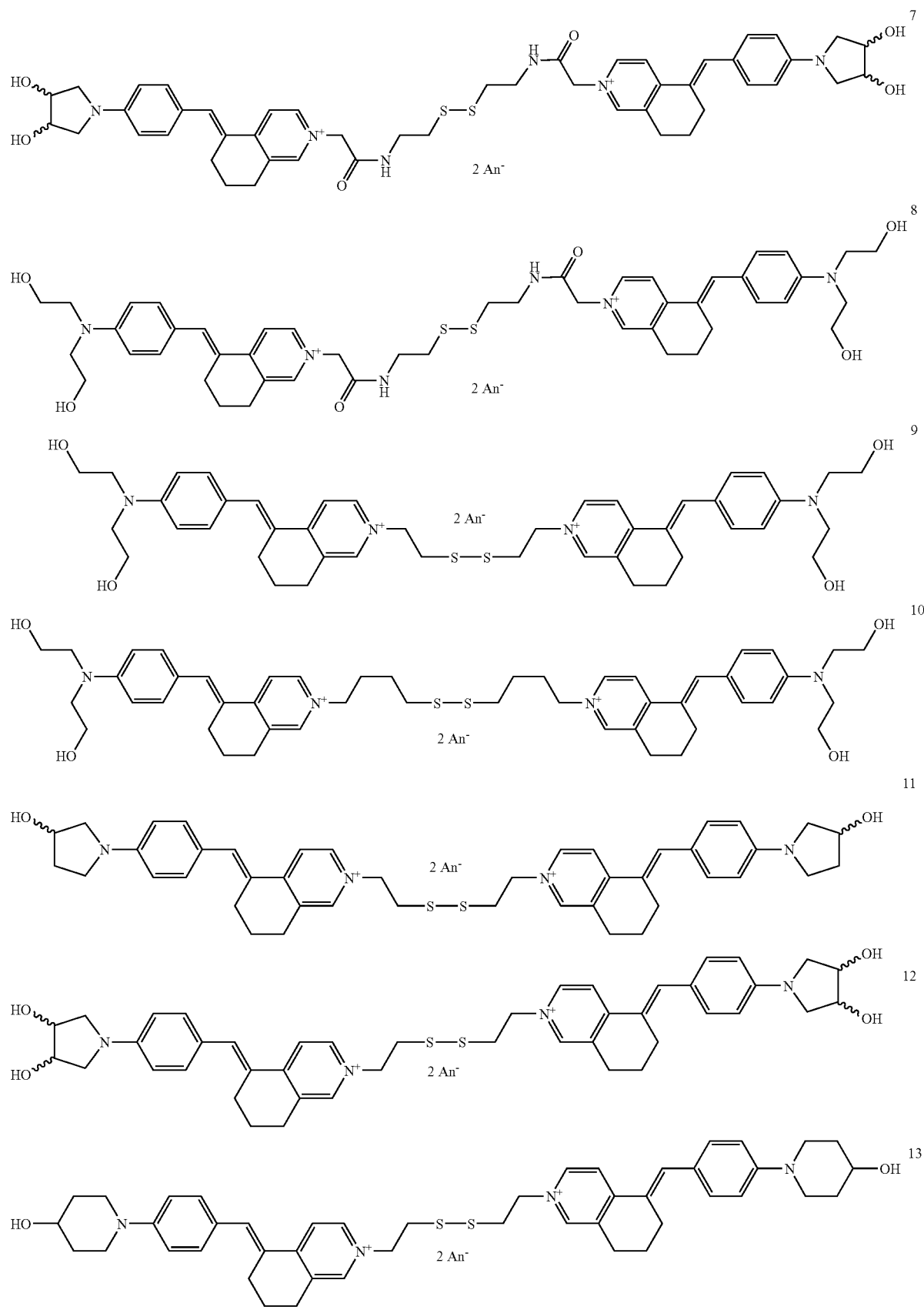

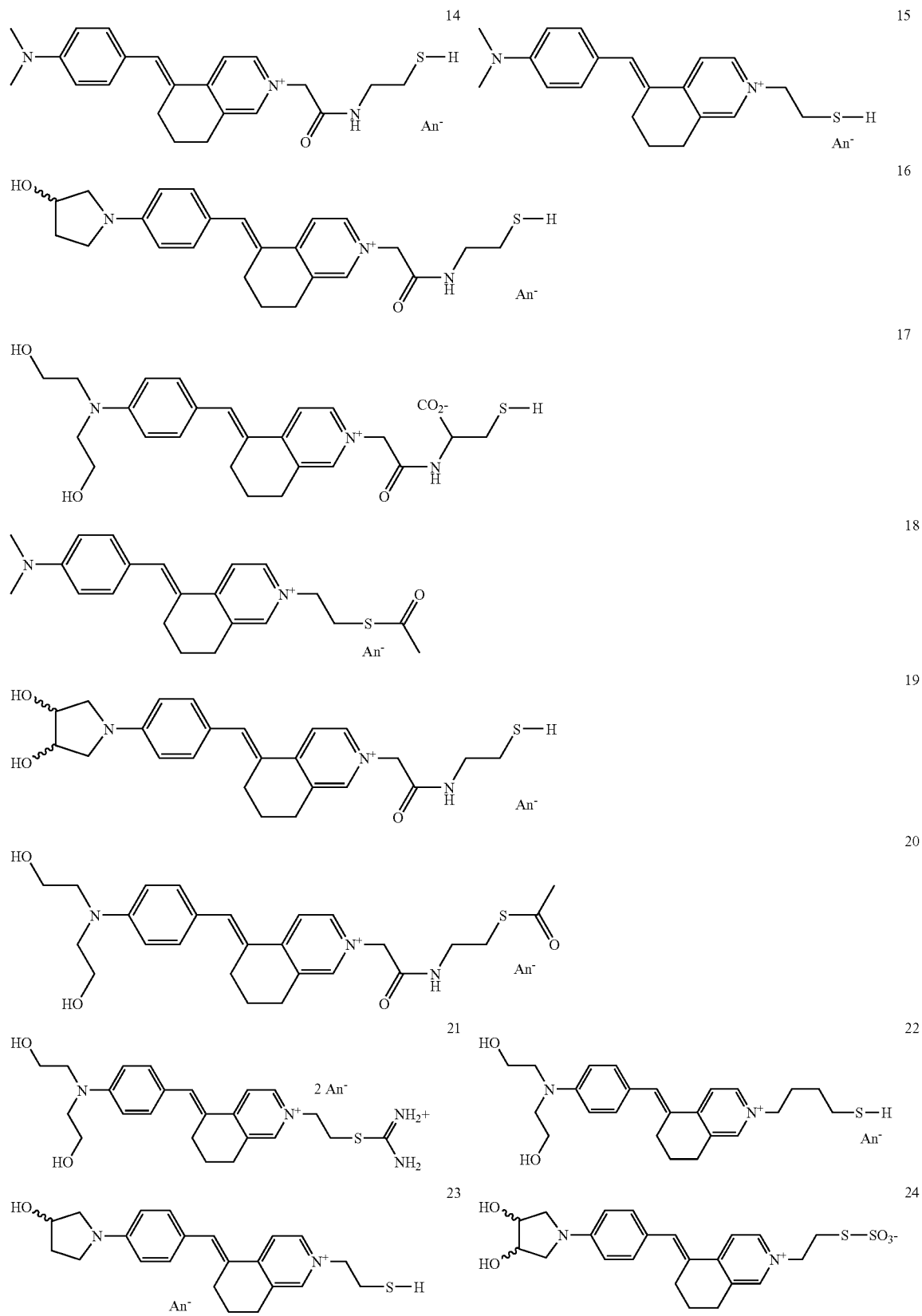

-continued

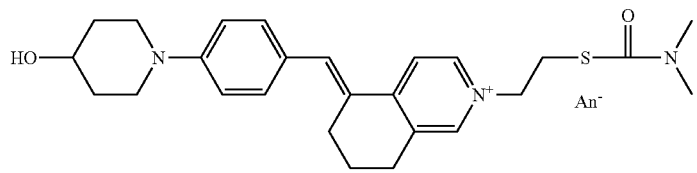

25

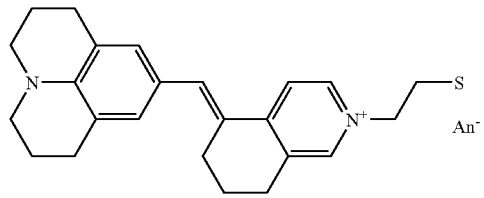

26

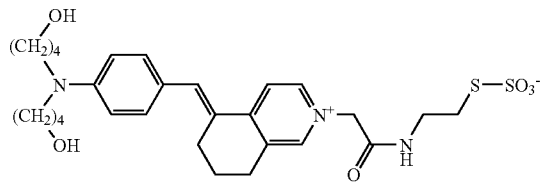

27

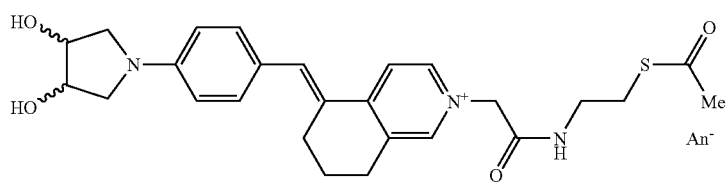

28

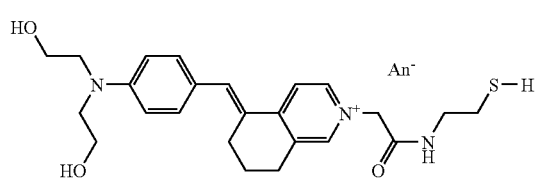

29

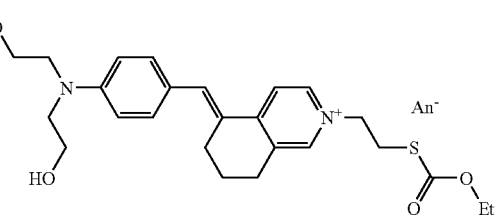

30

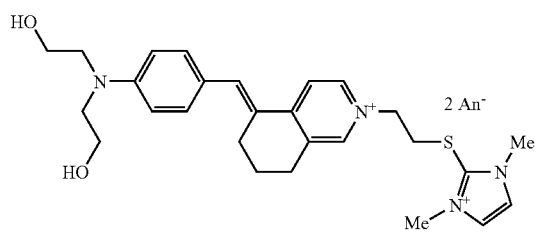

31

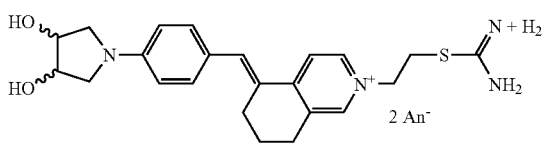

32 with An⁻, which may be identical or different, is an anionic counterion.

The protected thiol dyes of formula (II') can be synthesized in two stages. The first stage may comprise in preparing the nonprotected thiol dye (II'') according to the methods known to those skilled in the art, for instance "*Thiols and organic sulfides*", "*Thiocyanates and isothiocyanates, organic*", Ullmann's Encyclopedia, Wiley-VCH, Weinheim, 2005. In addition, the second step may comprise in protecting the thiol function according to the conventional methods known to those skilled in the art in order to produce the protected thiol dyes of formula (II'). By way of non-limiting example, for protecting the thiol function —SH of the thiol dye, use may be made of the methods in the books "*Protective Groups in Organic Synthesis*", T. W. Greene, John Wiley & Sons Ed., NY, 1981, pp. 193-217; "*Protecting Groups*", P. Kocienski, Thieme, 3rd Ed., 2005, Chap. 5.

This method can be illustrated, for example, by means of the method comprising i) in generating thiol fluorescent dyes of formula (II'') by reduction of a heterocyclic, two-chromophore fluorescent dye bearing a disulfide function —S—S— such as (I') and ii) in protecting said thiol function of (II''), according to methods known by a skilled artisan, with the reactant 7 Y'R in order to obtain the protected thiol fluorescent dyes of formula (II'). The thiol compound (II'') may also be metallated with an alkali metal or alkaline earth metal Met* so as to produce the thiolate fluorescent dye of formula (II''').

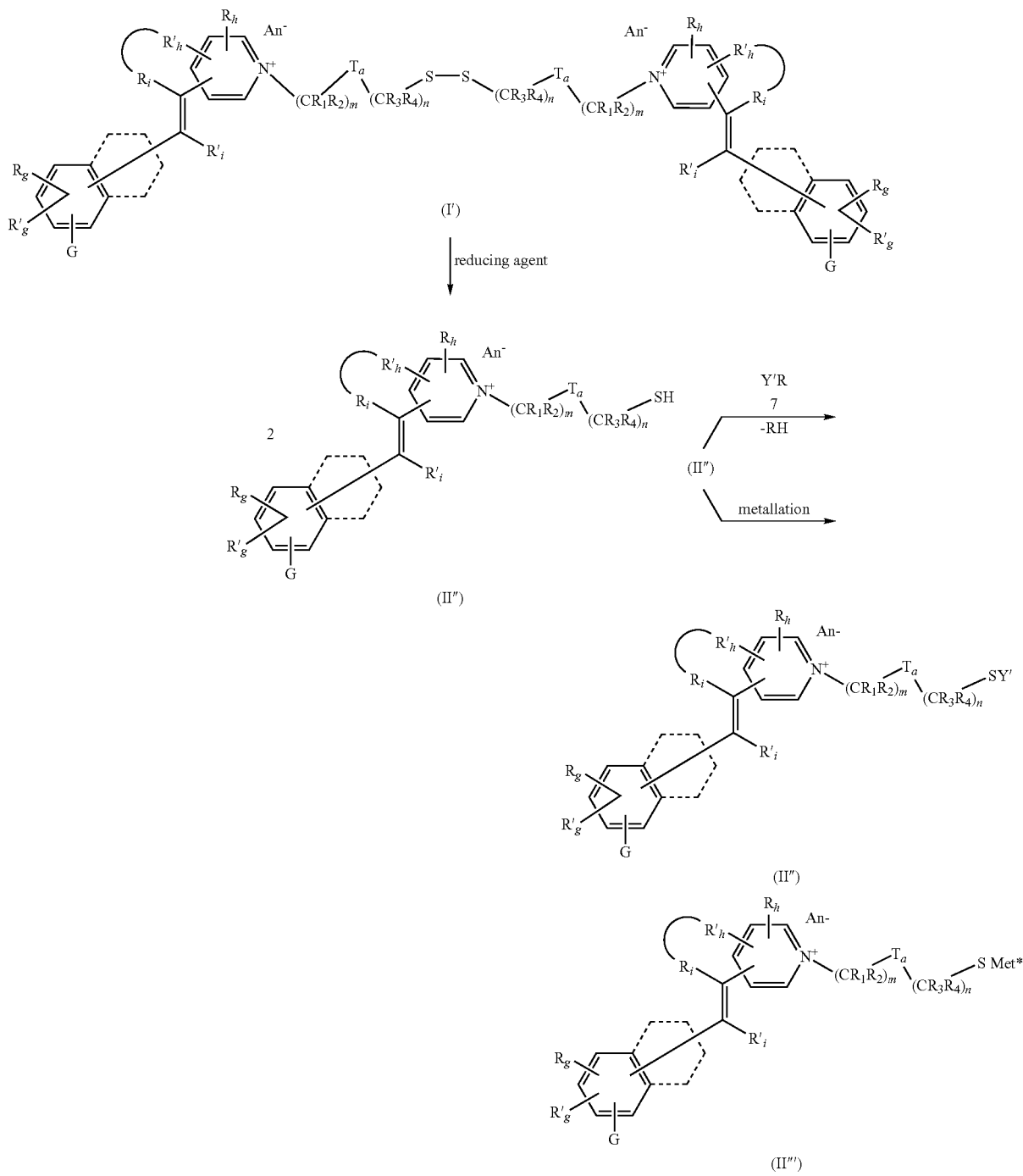

wherein Y' comprises a thiol-function-protecting group; Met* comprises an alkali metal or an alkaline earth metal, such as sodium or potassium, it being understood that, when the metal is an alkaline earth metal, 2 chromophores comprising a thiolate —S⁻ function can be associated with 1 Metal²⁺;

wherein $R_1$, $R_2$, $R_3$, $R_4$, $R_g$, $R'_g$, $R_h$, $R'_h$, $R_i$, $R'_i$, m, n, G, and An⁻ are as defined above; Y' comprises a thiol-function-protecting group; and R comprises a nucleofuge leaving group, for instance mesylate, tosylate, triflate, or halide.

In another embodiment, a protected thiol compound (b) protected with a protecting group Y' as defined above, prepared according to one of the procedures described in the books described above, said protected thiol compound comprising at least one nucleophilic function, can be reacted with a sufficient, such as equimolar, amount of a "reactive fluorescent chromophore" or of a compound comprising such a "reactive fluorescent chromophore" (a). In other words, (a) comprises an electrophilic function so as to form a linking group or a Σ covalent bond, as can be shown schematically below in the preparation of fluorescent dyes of formula (II'):

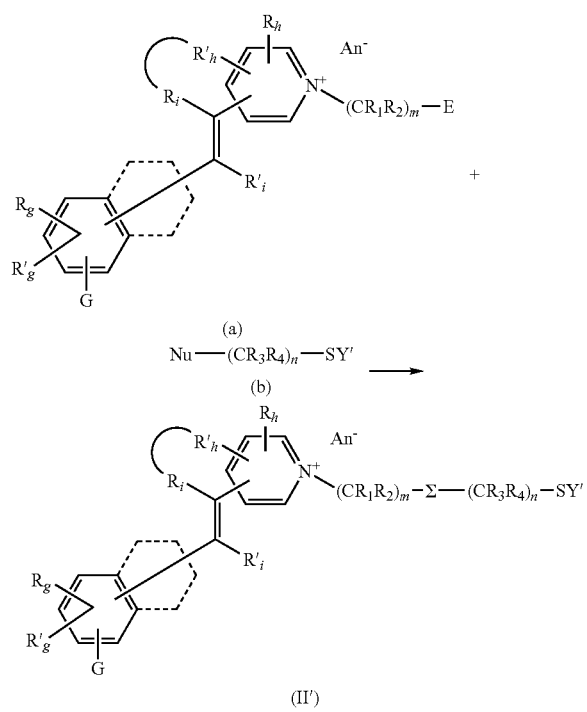

(a)

Nu—(CR$_3$R$_4$)$_n$—SY'

(b)

(II')

wherein R$_1$, R$_2$, R$_3$, R$_4$, R$_g$, R'$_g$, R$_h$, R'$_h$, R$_i$, R'$_i$, m, n, G, Y', and An$^-$ are as defined above; Nu is a nucleophilic group; E is an electrophilic group; and Σ the linking group generated after attack by the nucleophile on the electrophile, it being understood that Σ is a subset of the definition of Ta as described in formulae (I) and (II).

In one aspect, the Σ covalent bonds that can be generated are listed in the table below based on condensation of electrophiles with nucleophiles:

| Electrophiles E | Nucleophiles Nu | Σ Covalent bonds |
|---|---|---|
| Activated esters* | Amines | Carboxamides |
| Acyl nitrides** | Amines | Carboxamides |

-continued

| Electrophiles E | Nucleophiles Nu | Σ Covalent bonds |
|---|---|---|
| Acyl halides | Amines | Carboxamides |
| Acyl halides | Alcohols | Esters |
| Acyl cyanides | Alcohols | Esters |
| Acyl cyanides | Amines | Carboxamides |
| Alkyl halides | Amines | Alkylamines |
| Alkyl halides | Carboxylic acids | Esters |
| Alkyl halides | Thiols | Thioesters |
| Alkyl halides | Alcohols | Ethers |
| Sulfonic acids and salts thereof | Thiols | Thioethers |
| Sulfonic acids and salts thereof | Carboxylic acids | Esters |
| Sulfonic acids and salts thereof | Alcohols | Ethers |
| Anhydrides | Alcohols | Esters |
| Anhydrides | Amines | Carboxamides |
| Aryl halides | Thiols | Thioethers |
| Aryl halides | Amines | Arylamines |
| Aziridines | Thiols | Thioethers |
| Carboxylic acids | Amines | Carboxamides |
| Carboxylic acids | Alcohols | Esters |
| Carbodiimides | Carboxylic acids | N-acylureas |
| Diazoalkanes | Carboxylic acids | Esters |
| Epoxides | Thiols | Thioethers |
| Haloacetamides | Thiols | Thioethers |
| Imide esters | Amines | Amidines |
| Isocyanates | Amines | Ureas |
| Isocyanates | Alcohols | Urethanes |
| Isothiocyanates | Amines | Thioureas |
| Maleimides | Thiols | Thioethers |
| Sulfonic esters | Amines | Alkylamines |
| Sulfonic esters | Thiols | Thioethers |
| Sulfonic esters | Carboxylic acids | Esters |
| Sulfonic esters | Alcohols | Ethers |
| Sulfonyl halides | Amines | Sulfonamides |

*the activated esters of general formula —CO-Part with Part representing a leaving group such as oxysuccinimidyl, oxybenzotriazolyl, aryloxy which is optionally substituted;
**the acyl nitrides may rearrange to give isocyanates.

Another embodiment of this process is to use a fluorescent chromophore having an electrophilic acrylate function (—OCO—C=C—) on which is carried out an addition reaction that will generate a Σ bond.

It is also possible to use a thiol reactant (α): Y'—SH comprising a Y' group as defined above, the nucleophilic SH function of which can react with the carbon atom in the α-position with respect to the halogen atom borne by a fluorescent chromophore, so as to give the protected thiol fluorescent dye of formula (II'):

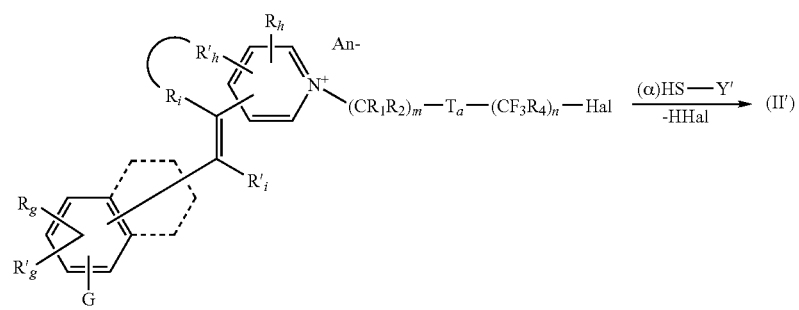

wherein $R_1$, $R_2$, $R_3$, $R_4$, $R_g$, $R'_g$, $R_h$, $R'_h$, $T_a$, $R_i$, $R'_i$, m, n, G, Y', (II'), and An⁻ are as defined above, and Hal is chosen from a nucleofuge halogen atom such as bromine, iodine, or chlorine.

For example, a nucleofuge leaving group may be replaced with a derivative of a thiourea (S=C(NRR)NRR), or thiourea, so as to generate isothiouroniums. For example, if the thiourea derivative is a thioimidazolinium (β), the reaction scheme is the following:

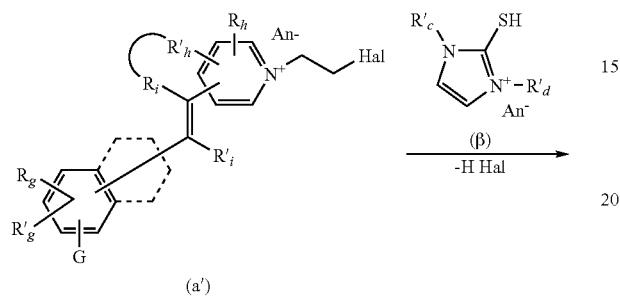

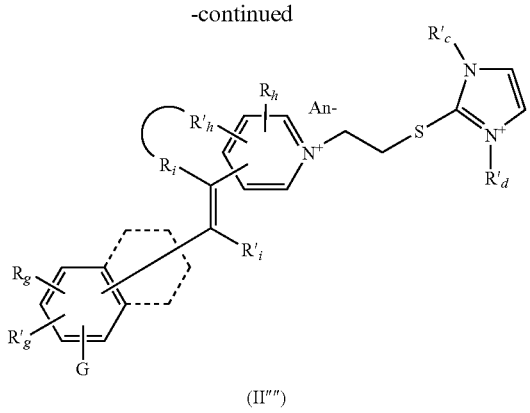

wherein $R'_c$, $R'_d$, $R_g$, $R'_g$, $R_h$, $R'_h$, $R_i$, $R'_i$, m, n, G, Hal, and An⁻ are as defined above.

Another aspect is to obtain the compound (II'''' sat) using a cyclic thiourea derivative of imidazoline type (b'), followed by alkylation of said imidazoline using $R'_d$-Lg, with Lg being a leaving group such as chloride, bromide, tosylate, or mesylate:

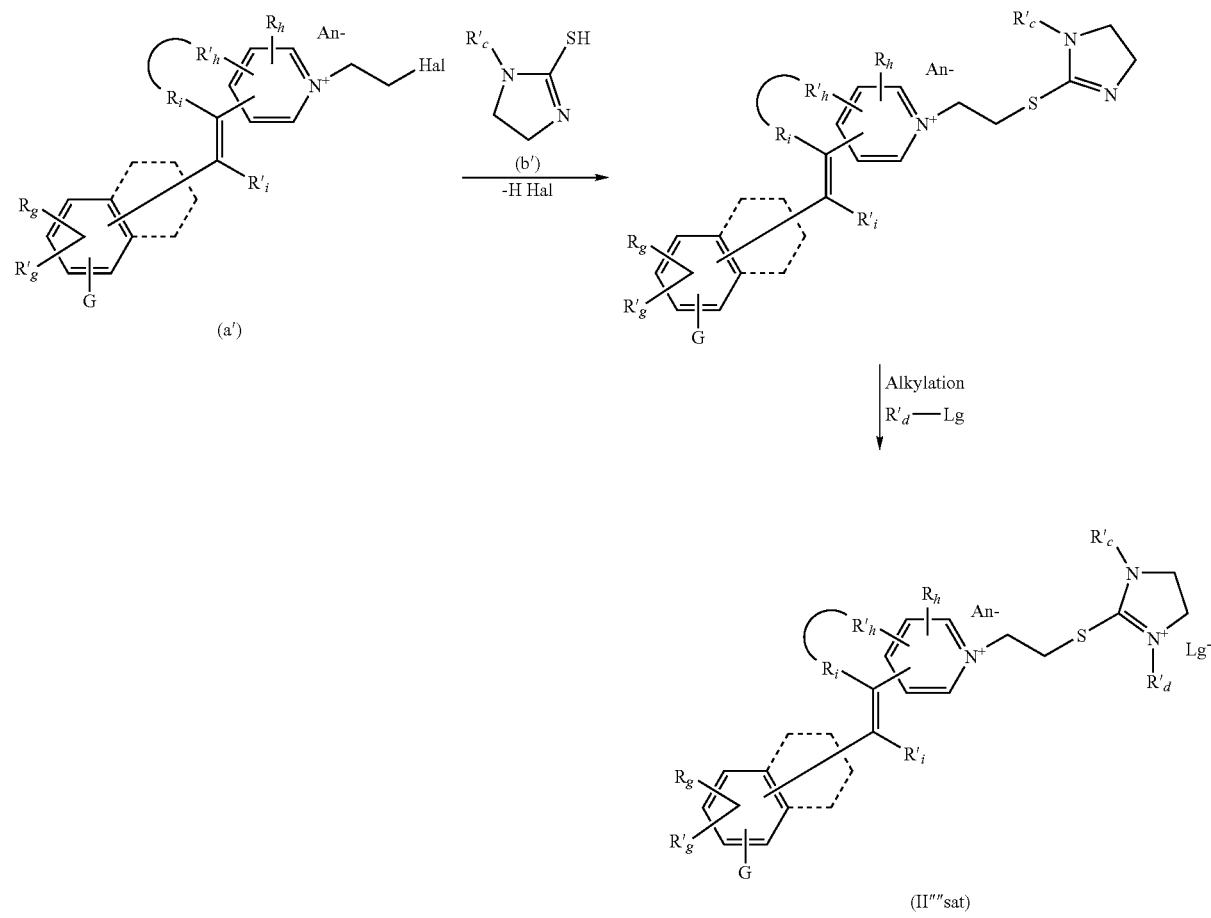

wherein R'$_c$, R'$_d$, R$_g$, R'$_g$, R$_h$, R'$_h$, R$_i$, R'$_i$, m, n, G, Hal, and An$^-$ are as defined above.

One embodiment is to use, in place of the halide comprising the fluorescent chromophore (a'), a chromophore comprising another type of nucleofuge such as tosylate or mesylate.

In at least another embodiment, certain protected thiol fluorescent dyes (II') can be obtained by reacting a protected thiol compound with a compound bearing two carboxylic acid functions that are activated, according to the conventional methods (for example, reaction with a carbodiimide or with thionyl chloride). The resulting product (d) is subsequently reacted with a fluorescent chromophore bearing a nucleophilic function (c), for example of primary or secondary amine type, or of aliphatic alcohol type.

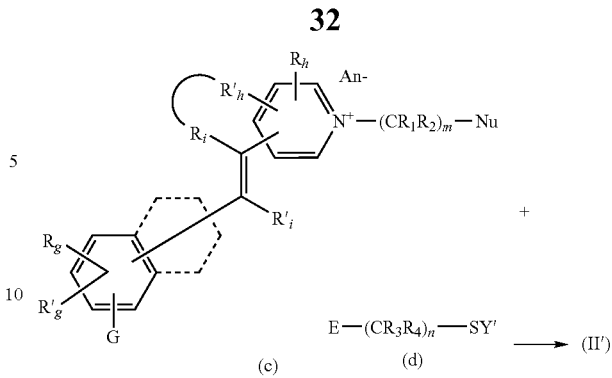

wherein R$_1$, R$_2$, R$_3$, R$_4$, R$_g$, R'$_g$, R$_h$, R'$_h$, R$_i$, R'$_i$, G, T$_a$, Y', m, n, AN-, E, Nu, and (II') are as defined above.

Another aspect is to use a thiolactone derivative as represented by the scheme below:

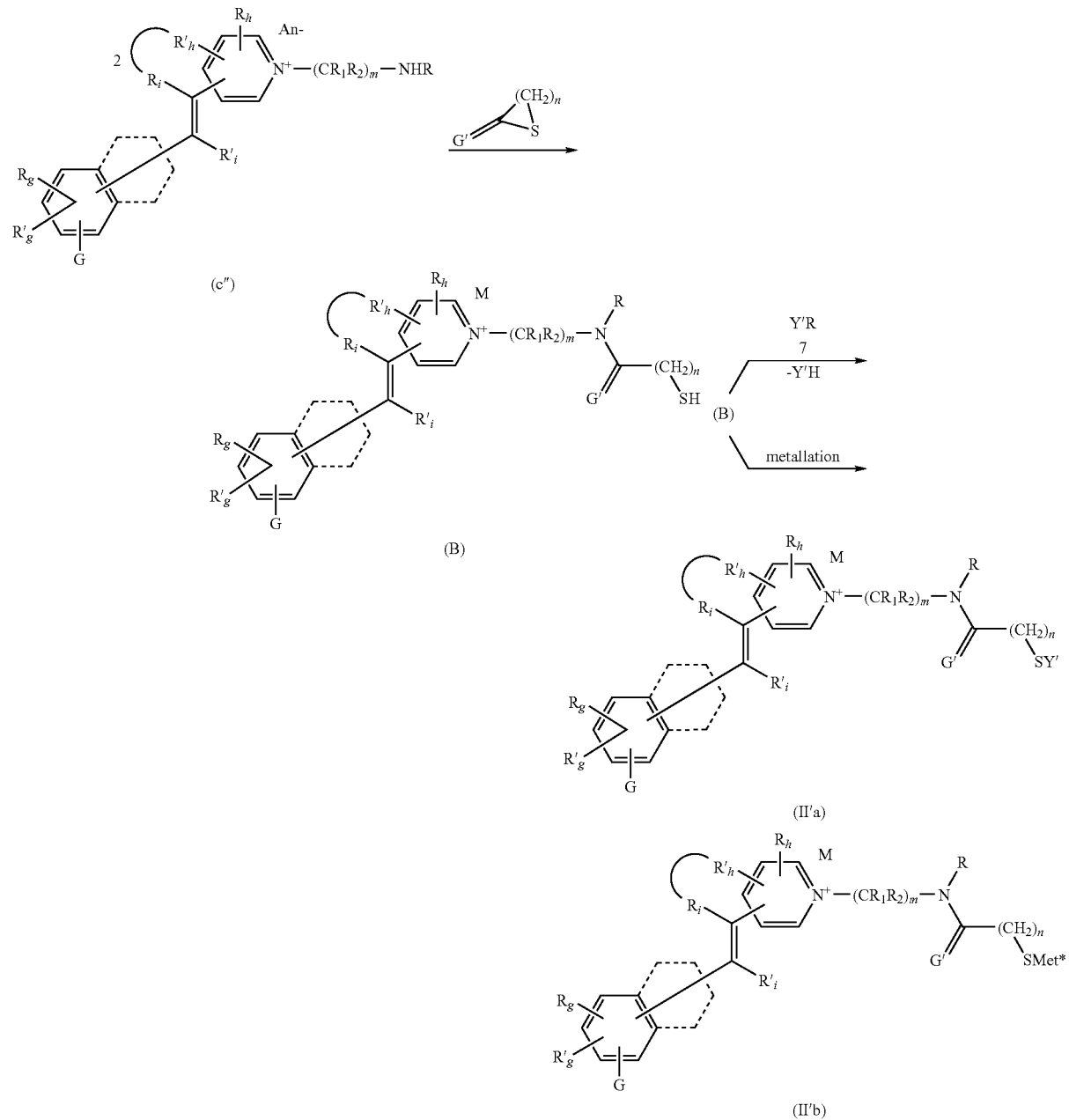

wherein $R_1$, $R_2$, $R_g$, $R'_g$, $R_h$, $R'_h$, $R_i$, $R'_i$, G, $T_a$, Y', Met*, n, m, and An⁻ are as defined above, G' is chosen from an oxygen atom, a sulfur atom, and an NR' group, wherein R' is chosen from a hydrogen atom and a alkyl radical, and R is chosen from a hydrogen atom, a $C_1$-$C_4$ alkyl radical, a $C_1$-$C_4$ hydroxyalkyl radical, and an aryl($C_1$-$C_4$)alkyl. For example, the thiolactone is chosen with n=3 and G' is an oxygen atom.

One synthesis embodiment is to combine the above pathway with the first pathway, i.e., using two equivalents of the nucleophile reactant (c) with a dielectrophilic disulfide reactant (i), it is possible to generate, after condensation, the dichromophoric disulfide product (I″), it being possible for the latter to undergo a reduction so as to form the heterocyclic fluorescent thiol dye which, in turn, may be either protected so as to form the protected thiol fluorescent dye in (II′) or metallated with an alkali metal so as to give the metallated heterocyclic thiol fluorescent dye (II‴):

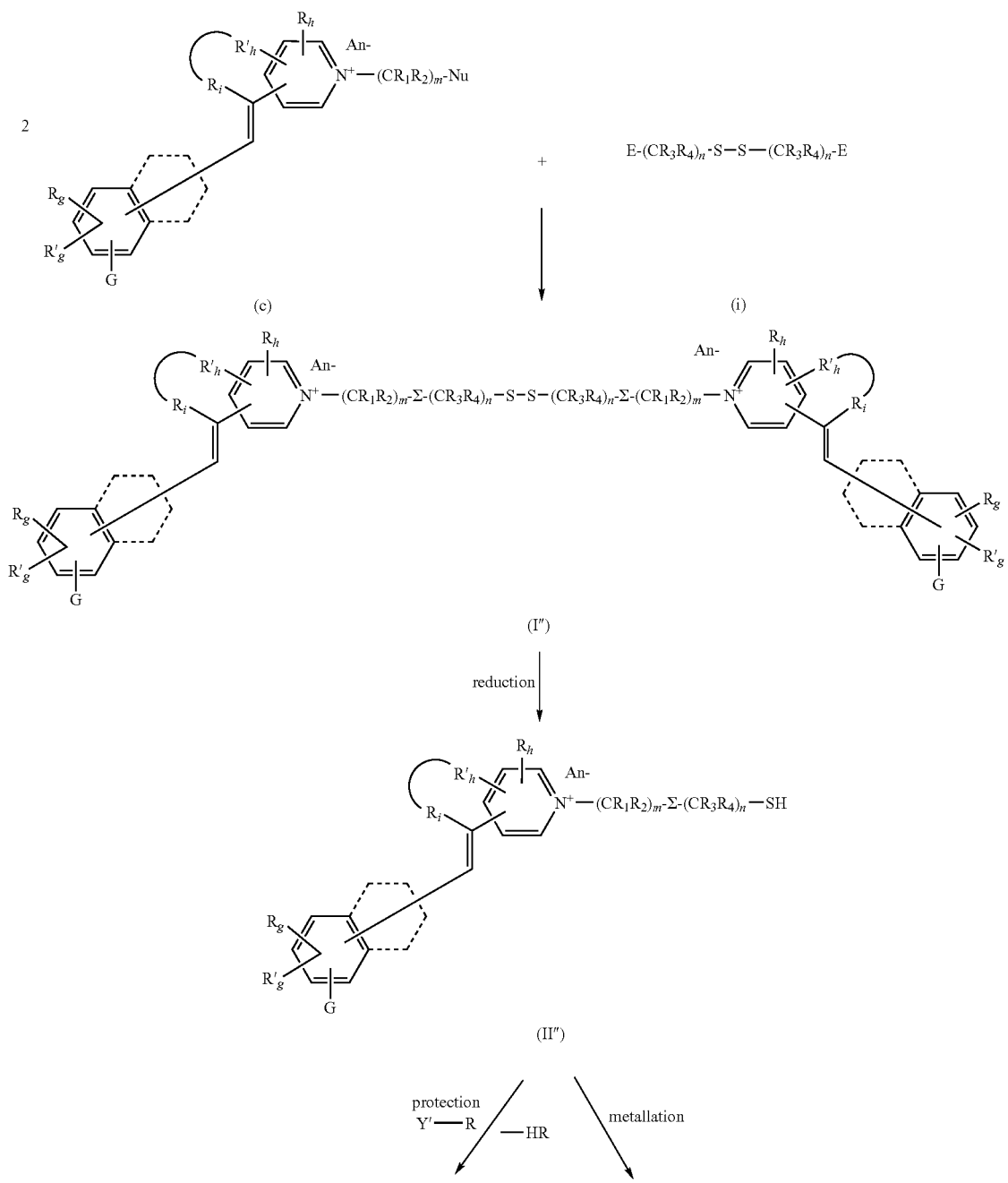

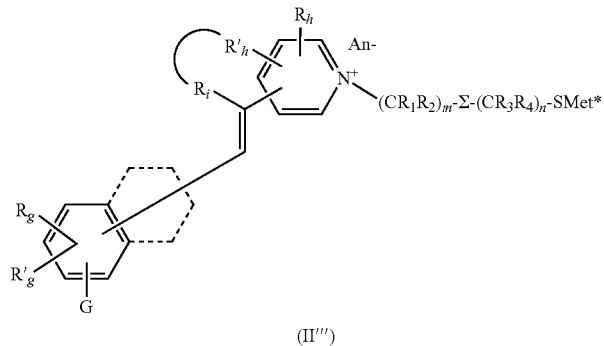

(II')

wherein $R_1$, $R_2$, $R_3$, $R_4$, $R_g$, $R'_g$, $R_h$, $R'_h$, $R_i$, $R'_i$, G, E, Nu, $\Sigma$, Y', Met*, n, m, and An⁻ are as defined above.

In yet another embodiment, the protected thiol fluorescent dyes of formula (II') can be obtained by reaction of a compound comprising a thiol group protected with a Y' group, and a hydroxyl group activated beforehand to a nucleofuge leaving group (d'), for instance mesylate, tosylate, triflate, or halide, with a styrylpyridine chromophore (c').

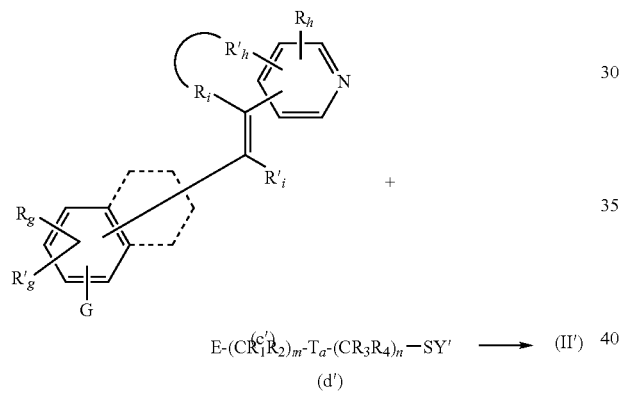

(c')

$$E-(CR_1R_2)_m-T_a-(CR_3R_4)_n-SY' \longrightarrow (II')$$
(d')

wherein $R_1$, $R_2$, $R_3$, $R_4$, $R_g$, $R'_g$, $R_h$, $R'_h$, $R_i$, $R'_i$, G, $T_a$, Y', m, n, (II'), and E are as defined above.

By way of non-limiting example, a compound containing a protected thiol group comprising a nucleofuge leaving group R, for instance mesylate, tosylate, or triflate, which can undergo nucleophilic attack from the amine borne by the styryl fluorescent chromophore:

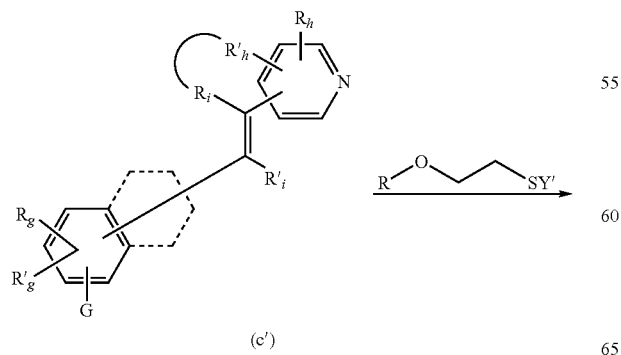

(c')

-continued

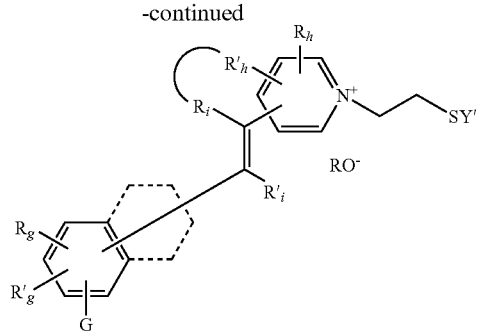

wherein $R_g$, $R'_g$, $R_h$, $R'_h$, $R_i$, $R'_i$, G, R, and Y' are as defined above.

Another embodiment comes from the use of halides as nucleofuge leaving group on a thiol compound that can be substituted with a primary amine function, for example, borne by a styryl fluorescent chromophore:

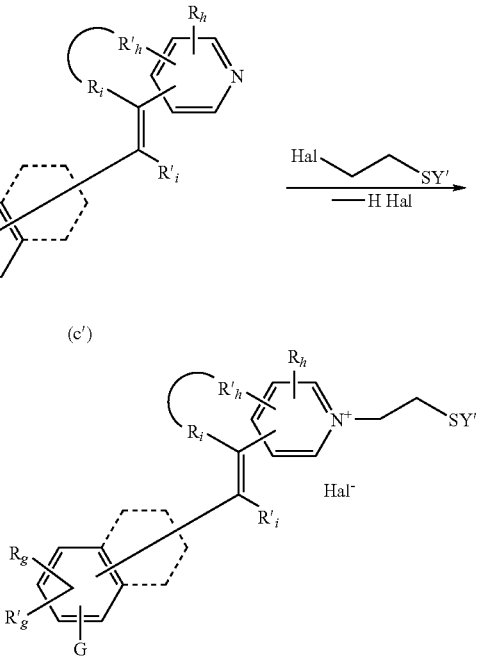

wherein $R_g$, $R'_g$, $R_h$, $R'_h$, $R_i$, $R'_i$, G, and Y' are as defined above.

In accordance with another embodiment, the thiol fluorescent dyes of formula (II) according to the present disclosure can be obtained by reaction of a compound comprising a thiol group Y as defined above and an electrophilic group (f), with a pyridinium compound comprising a nucleophilic group. By way of non-limiting example, an aldehyde or a thioaldehyde when G' is chosen from an oxygen atom and a sulfur atom may be condensed with an "activated methylene" such as alkylpyridinium (e) so as to generate an ethylene bond >C=C<. This reaction is commonly known as "Knoevenagel" condensation. As used herein, "activated methylenes" means those which comprise, for example, in the 2- or 4-position with respect to the pyridinium group, a methylene group $R_i$—$CH_2$—:

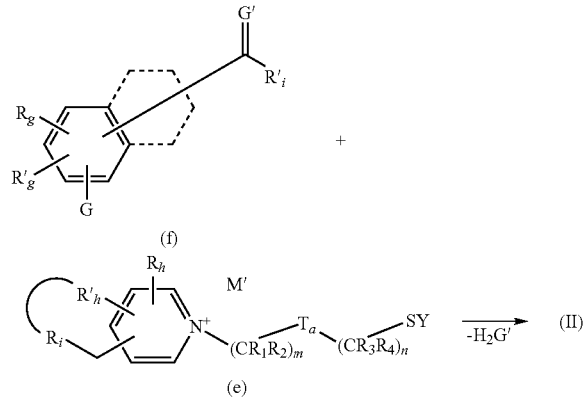

wherein $R_1$, $R_2$, $R_3$, $R_4$, $R_a$, $R_b$, $R_g$, $R'_g$, $R_h$, $R'_h$, $R_i$, $R'_i$, $T_a$, m, n, Y, and $An^-$ are as defined above and G is chosen from an oxygen atom and a sulfur atom.

Reference may be made to the book *Advanced Organic Chemistry*, "Reactions, Mechanisms and Structures", J. March, 4th Ed., John Wiley & Sons, 1992 or T. W. Greene "*Protective Groups in Organic Synthesis*", for further details on the operating conditions used for the processes mentioned above.

The thiol fluorescent dyes formed can be converted to —SY' protected thiol fluorescent dyes by protection of the —SH thiol using the conventional protecting groups. The thiol fluorescent dyes are metallated by also using the conventional methods known to those skilled in the art, such as those described in *Advanced Organic Chemistry*, "Reactions, Mechanisms and Structures", J. March, 4th Ed., John Wiley & Sons, NY, 1992.

The protected thiol dyes can be deprotected by conventional pathways such as those described in the books "*Protective Groups in Organic Synthesis*", T. W. Greene, John Wiley & Sons Ed., NY, 1981; "*Protecting Groups*", P. Kocienski, Thieme, 3rd Ed., 2005.

The starting reactants are commercially available or accessible by conventional methods known to those skilled in the art. By way of non-limiting example, reactant (I') can be synthesized using two equivalents of pyridine derivative 1 and one equivalent of disulfide reactant comprising two leaving groups Lg, so as to give the dipyridinium disulfide salt 3 which can, in turn, condense with two equivalents of aryl compound comprising an aldehyde/thioaldehyde group 4, so as to give 5.

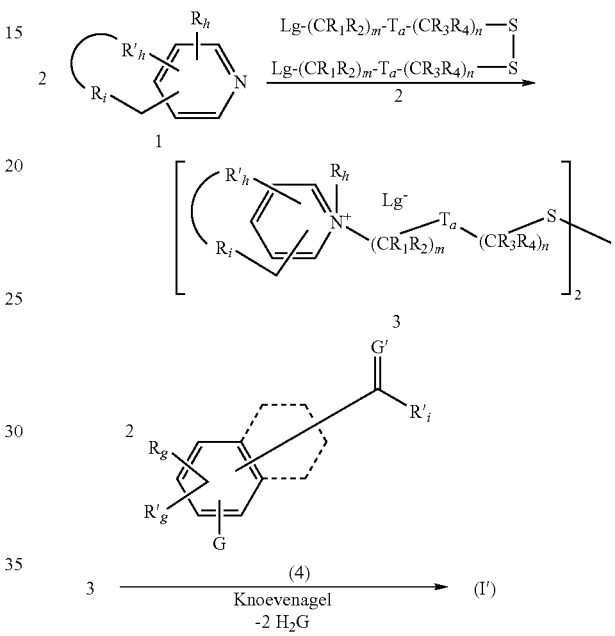

wherein $R_g$, $R'_g$, $R_h$, $R'_h$, $R_i$, $R'_i$, m, n, $T_a$, G, G', $R_1$, $R_2$, $R_3$, and $R_4$ are as defined above; Lg being a nucleofuge leaving group, for instance mesylate, tosylate, triflate, or halide. The counterions $Lg^-$ of the compounds (I') above can be replaced with counterions $An^-$ of other natures using methods known to those skilled in the art, such as by ion-exchange resin.

In at least one embodiment, the dissymmetric disulfide dyes of formula (I) can be synthesized in one stage by reacting a nonprotected thiol fluorescent dye with a thiol fluorescent dye protected with Y', so as to form the disulfide dye of formula (I).

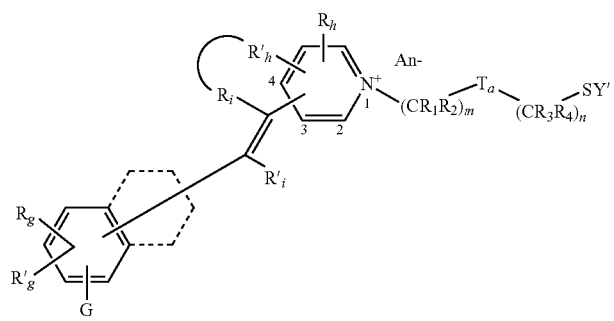

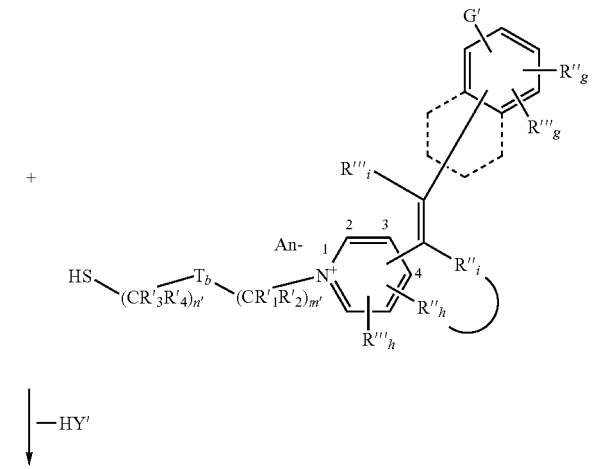

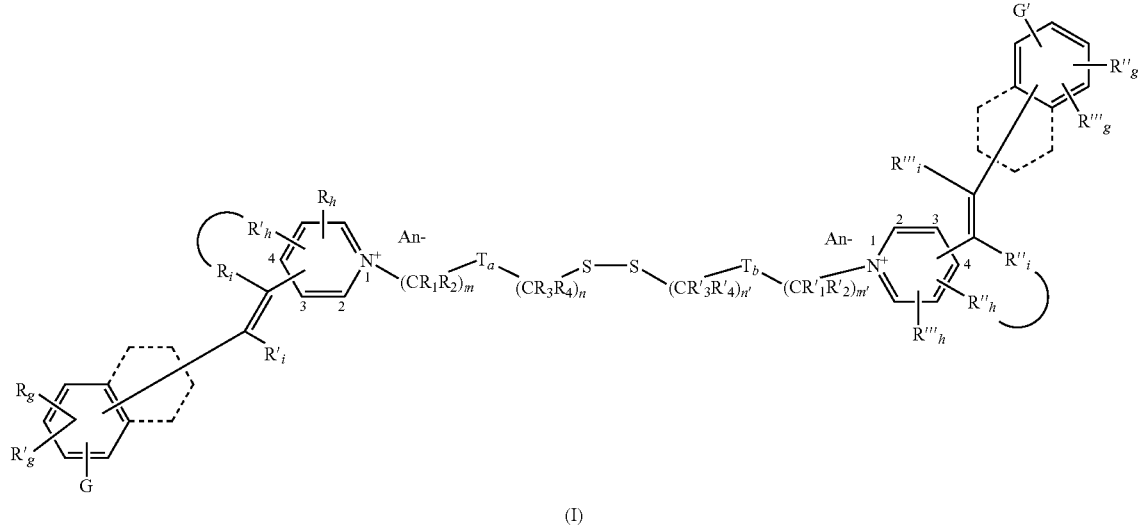

(I)

wherein $R_g$, $R'_g$, $R''_g$, $R'''_g$, $R_h$, $R'_h$, $R''_h$, $R'''_h$, $R_i$, $R'_i$, $R''_i$, m, m', n, n', $T_a$, $T_b$, G, G', Het, and $An^-$ are as defined above; Y' is a thiol-function-protecting group.

In at least one embodiment, the symmetrical fluorescent disulfide dyes of formula (I') can be synthesized by oxidation of the hemicyanin thiol dyes (II).

The oxidation can be carried out with an oxidizing agent, which can optionally be associated. Any oxidizing agent that is conventional in the field may be used. Thus, it may be chosen, for example, from hydrogen peroxide, urea peroxide, alkali metal bromates, persalts such as perborates and persulfates, and also enzymes, among which non-limiting mention may be made of peroxidases, 2-electron oxidoreductases such as uricases, and 4-electron oxygenases such as laccases. For example, hydrogen peroxide may be used.

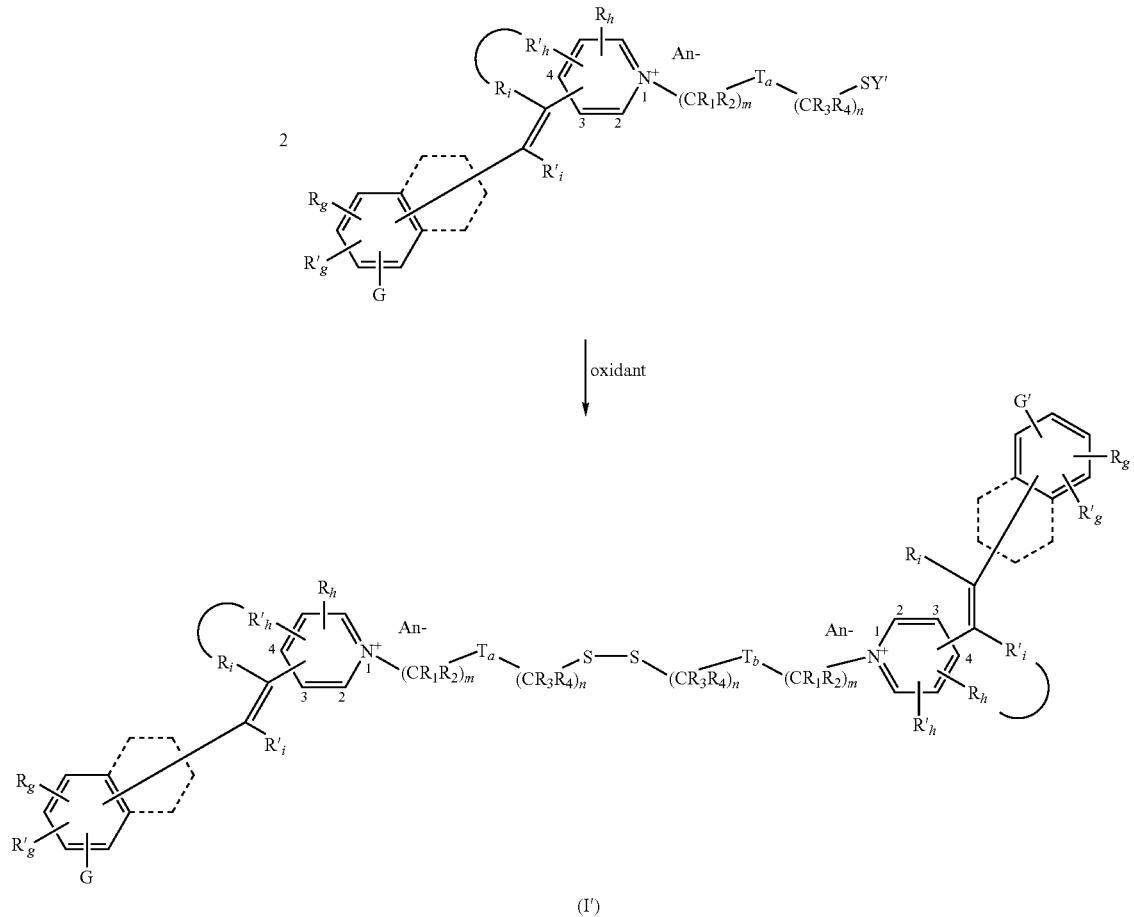

(I')

wherein $R_g$, $R'_g$, $R''_g$, $R'''_g$, $R_h$, $R'_h$, $R''_h$, $R'''_h$, $R_i$, $R'_i$, $R''_i$, $R'''_i$, m, m', n, n', $T_a$, $T_b$, G, G', and $An^-$ are as defined above; Y' is chosen from a hydrogen atom and an alkali metal, optionally a thiol-protecting group in the case where this group can be deprotected with an oxidizing agent or an alkaline agent (such as, acyl groups).

In at least one other embodiment, a disulfide compound (b1), said disulfide compound comprising two nucleophilic functions, can be reacted with a sufficient amount, such as two equivalents, of a hemicyanin styryl chromophore (a1), and which comprises an electrophilic function so as to form a Σ covalent linking group; see below, the preparation of dyes of formula (I')

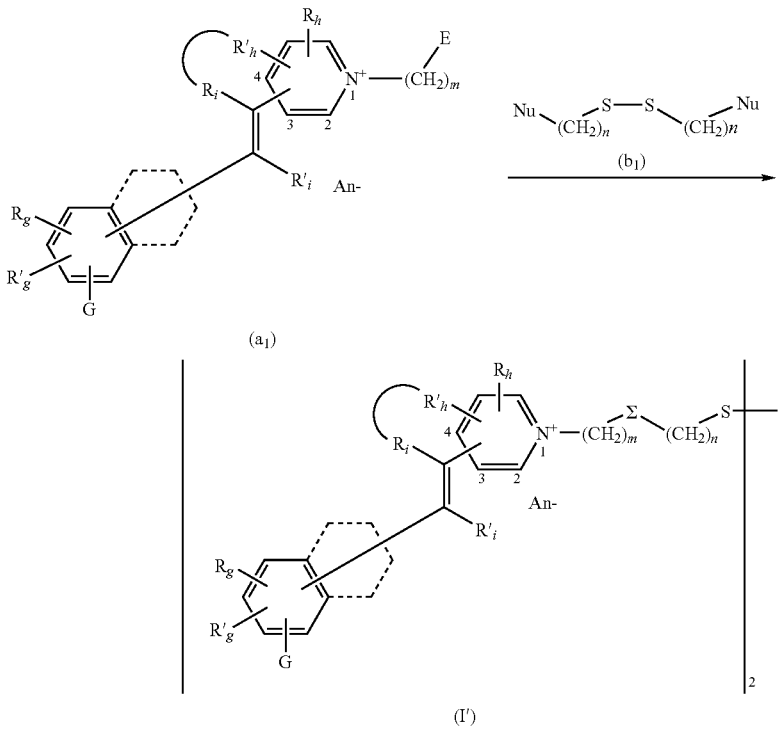

wherein $R_g$, $R'_g$, $R_h$, $R'_h$, $R_i$, $R'_i$, m, n, G, $An^-$, Σ, E, and Nu are as defined above, it being understood that Σ is chosen from a subset of Ta defined in formulae (I) and (II).

One aspect of this process is to use a hemicyanin styryl chromophore having an electrophilic acrylate function (—OCO—C=C—) on which is carried out an addition reaction that will generate a covalent bond in a Σ linking group.

In accordance with another aspect, the disulfide dyes of formula (I') can be obtained by reaction of a compound (b2) comprising a disulfide group and two nucleofuge leaving groups Lg, for instance mesylate, tosylate, triflate, or halide, with a hemicyanin styryl chromophore (a2) bearing a group X-Z'.

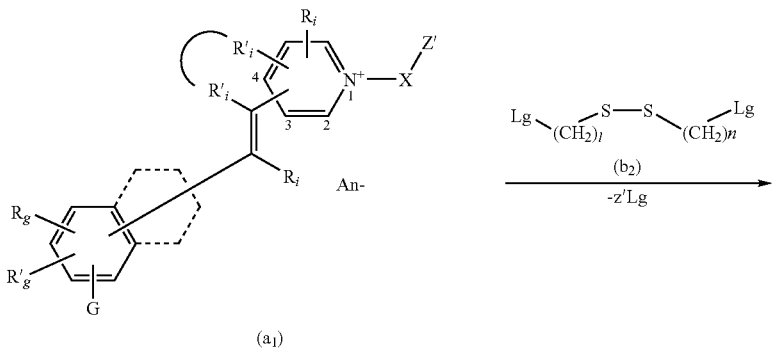

-continued

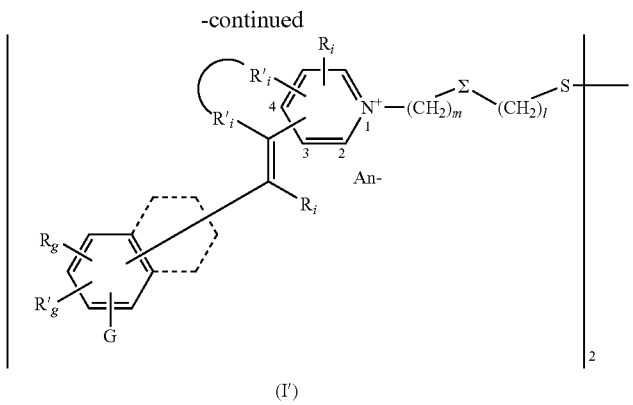

(I')

wherein $R_g$, $R'_g$, $R_h$, $R'_h$, $R_i$, $R'_i$, m, n, G, An$^-$, $\Sigma$, and z' are chosen from a hydrogen atom and an alkali metal, X-Z' are chosen from a hydrocarbon-based chain bearing a nucleophilic group capable of replacing the group Lg, for instance an amino or hydroxyl function, it still being understood that $\Sigma$ is chosen from a subset of Ta defined in formulae (I) and (II).

The starting reactants are commercially available or accessible by conventional methods known to those skilled in the art.

Reference may be made to the book *Advanced Organic Chemistry*, "Reactions, Mechanisms and Structures", J. March, 4th Ed., John Wiley & Sons, 1992 or T. W. Greene "*Protective Groups in Organic Synthesis*", for further details on the operating conditions used for the processes mentioned above.

The thiol fluorescent dyes formed can be converted to —SY' protected thiol fluorescent dyes by protection of the —SH thiol using the conventional protecting groups. The thiol fluorescent dyes are metallated by also using the conventional methods known to those skilled in the art, such as those described in *Advanced Organic Chemistry*, "Reactions, Mechanisms and Structures", J. March, 4th Ed., John Wiley & Sons, NY, 1992.

The protected thiol dyes can be deprotected by conventional pathways such as those described in the books "*Protective Groups in Organic Synthesis*" T. W. Greene, John Wiley & Sons Publisher, NY, 1981; "*Protecting Groups*", P. Kocienski, Thieme, 3rd Ed., 2005.

Another aspect of the present disclosure relates to a dye composition for dyeing keratin materials, which contains at least one disulfide fluorescent dye of formula (I) or thiol fluorescent dye of formula (II). In addition to the presence of at least one fluorescent dye of formula (I) or (II), the composition of the present disclosure may also contain a reducing agent.

In one aspect, this reducing agent may be chosen from thiols, by way of non-limiting example cysteine, homocysteine, or thiolactic acid, the salts of these thiols, phosphines, bisulfite, sulfites, and thioglycolic acid and its esters, such as glyceryl monothioglycolate, and thioglycerol. This reducing agent may also be chosen, for example, from borohydrides and derivatives thereof, for instance the salts of borohydride, of cyanoborohydride, of triacetoxyborohydride, or of trimethoxyborohydride: sodium salts, lithium salts, potassium salts, calcium salts, quaternary ammonium (tetramethylammonium, tetraethylammonium, tetra-n-butylammonium, or benzyltriethylammonium) salts; and catechol borane.

The dye composition that can be used in the present disclosure may comprise an amount of fluorescent dye of formula (I) or (II) ranging from 0.001% to 50% relative to the total weight of the composition. For instance, this amount may range from 0.005% to 20% by weight, for example from 0.01% to 5% by weight, relative to the total weight of the composition.

The dye composition may also comprise additional direct dyes. These direct dyes are chosen, by way of non-limiting example, from neutral, acidic, or cationic nitrobenzene direct dyes, neutral, acidic, or cationic azo direct dyes, tetraazapentamethine dyes, neutral, acidic, or cationic quinone, such as anthraquinone dyes, azine direct dyes, triarylmethane direct dyes, indoamine direct dyes, and natural direct dyes.

Among the natural direct dyes, non-limiting mention may be made of lawsone, juglone, alizarin, purpurin, carminic acid, kermesic acid, purpurogallin, protocatechaldehyde, indigo, satin, curcumin, spinulosin, and apigenindin. Extracts or decoctions comprising these natural dyes, such as poultices or henna-based extracts, may also be used.

The dye composition may comprise at least one oxidation base and/or at least one coupler conventionally used for dyeing keratin fibers.

Among the oxidation bases, non-limiting mention may be made of para-phenylenediamines, bisphenylalkylenediamines, para-aminophenols, bis-para-aminophenols, ortho-aminophenols, heterocyclic bases, and addition salts thereof.

Among these couplers, non-limiting mention may be made of meta-phenylenediamines, meta-aminophenols, meta-diphenols, naphthalene couplers, heterocyclic couplers, and addition salts thereof.

The at least one coupler may be present in an amount ranging from 0.001% to 10% by weight, such as from 0.005% to 6% by weight, relative to the total weight of the dye composition.

The at least one oxidation base may be present in the dye composition in an amount ranging from 0.001% to 10% by weight, such as from 0.005% to 6% by weight, relative to the total weight of the dye composition.

For instance, the addition salts of the at least one oxidation base and of the at least one coupler that can be used in the context of the present disclosure are chosen, by way of non-limiting example, from addition salts with an acid, such as hydrochlorides, hydrobromides, sulfates, citrates, succinates, tartrates, lactates, tosylates, benzenesulfonates, phosphates, and acetates, and addition salts with a base, such as hydroxides of an alkali metal such as sodium or potassium, aqueous ammonia, amines, or alkanolamines.

The cosmetically acceptable medium for dyeing, also called dye support, is a cosmetic medium generally constituted of water or of a mixture of water and at least one organic solvent. By way of the at least one organic solvent, non-limiting mention may, for example, be made of $C_1$-$C_4$ lower alkanols, such as ethanol and isopropanol; polyols and polyol ethers, such as 2-butoxyethanol, propylene glycol, propylene glycol monomethyl ether, diethylene glycol monoethyl ether, and diethylene glycol monomethyl ether, and also aromatic alcohols such as benzyl alcohol or phenoxyethanol, and mixtures thereof.

The at least one solvent may be present in proportions ranging from approximately 1% to 99% by weight, for instance, from approximately 5% and 95% by weight, relative to the total weight of the dye composition.

In at least one embodiment, the composition of the present disclosure comprises a reducing agent capable of reducing the disulfide bonds of keratin and/or the disulfide bonds of the fluorescent dyes of formula (I). This reducing agent is as defined above.

The dye composition may also comprise various adjuvants conventionally used in hair-dyeing compositions, such as, by way of non-limiting example, anionic, cationic, nonionic, amphoteric, or zwitterionic surfactants or mixtures thereof, anionic, cationic, nonionic, amphoteric, or zwitterionic polymers, or blends thereof, mineral or organic thickeners, such as anionic, cationic, nonionic, and amphoteric associative polymer thickeners, antioxidants, penetrating agents, sequestering agents, fragrances, buffers, dispersing agents, conditioning agents such as, for example, modified or unmodified, volatile or nonvolatile silicones, such as amino silicones, film-forming agents, ceramides, preservatives, opacifiers, or conductive polymers.

The above adjuvants may be present in an amount, for each of them, ranging from 0.01% to 20% by weight relative to the weight of the composition.

Those skilled in the art will take care to select this or these possible additional compounds in such a way that the advantageous properties intrinsically associated with the dye composition in accordance with the present disclosure are not, or are not substantially, impaired by the addition(s) envisaged.

The pH of the dye composition can range from approximately 3 to 14, for example, from approximately 5 to 11. It may be adjusted to the desired value by means of at least one acidifying or basifying agent normally used in the dyeing of keratin fibers or else by means of conventional buffer systems.

Among the at least one acidifying agent, non-limiting mention may be made, by way of example, of mineral or organic acids, such as hydrochloric acid, orthophosphoric acid, sulfuric acid, carboxylic acids, for instance acetic acid, tartaric acid, citric acid, or lactic acid, or sulfonic acids.

Among the at least one basifying agent, non-limiting mention may, by way of example, be made of aqueous ammonia, alkali carbonates, alkanolamines such as mono-, di-, and triethanolamines, and also derivatives thereof, sodium hydroxide or potassium hydroxide and the compounds of formula (γ) below:

(γ)

wherein $W_a$ is a propylene residue optionally substituted with a hydroxyl group or a $C_1$-$C_4$ alkyl radical; $R_{a1}$, $R_{a2}$, $R_{a3}$, and $R_{a4}$, which may be identical or different, are chosen from hydrogen atoms, $C_1$-$C_4$ alkyl radicals, and $C_1$-$C_4$ hydroxyalkyl radicals.

The dye composition may be in various forms, such as in the form of a liquid, a cream or a gel, or in any other form suitable for dyeing keratin fibers, such as the hair.

Another aspect of the present disclosure is a process for dyeing keratin material comprising applying a composition comprising at least one dye of formula (I) or (II) to said materials. According to at least one embodiment, in the process of the present disclosure, a reducing agent may also be applied as a pretreatment before the application of the composition comprising at least one fluorescent dye of formula (I) or (II).

This reducing agent may be chosen, by way of non-limiting example, from thiols, for example cysteine, homocysteine or thiolactic acid, the salts of these thiols, phosphines, bisulfite, sulfites, and thioglycolic acid and also its esters, for instance glyceryl monothioglycolate, and thioglycerol. This reducing agent may also be chosen, by way of non-limiting example, from borohydrides and derivatives thereof, for instance the salts of borohydride, of cyanoborohydride, of triacetoxyborohydride or of trimethoxyborohydride: sodium salts, lithium salts, potassium salts, calcium salts, quaternary ammonium (tetramethylammonium, tetraethylammonium, tetra-n-butylammonium, or benzyltriethylammonium) salts; and catechol borane.

This pretreatment may be of short duration, such as from 0.1 second to 30 minutes, for example, from 1 minute to 15 minutes, with a reducing agent as mentioned above.

According to another process of the present disclosure, the composition comprising at least one fluorescent dye of formula (I) or (II) also comprises at least one reducing agent as defined above. This composition is then applied to the hair.

When the thiol fluorescent dye of formula (II) comprises a thiol-function-protecting group Y, the process of the present disclosure may be preceded by a deprotection step aimed at restoring the SH function in situ.

By way of non-limiting example, it is possible to deprotect the S—Y function with a Y protecting group by adjusting the pH as follows:

| Y: Protecting group | Deprotection |
| --- | --- |
| alkylcarbonyl | pH > 9 |
| arylcarbonyl | pH > 9 |
| alkoxycarbonyl | pH > 9 |
| aryloxycarbonyl | pH > 9 |
| arylalkoxycarbonyl | pH > 9 |
| (di)(alkyl)aminocarbonyl | pH > 9 |
| (alkyl)arylaminocarbonyl | pH > 9 |
| optionally substituted aryl, such as phenyl | pH > 9 |
| 5-, 6- or 7-membered monocyclic heteroaryl such as oxazolium | pH > 9 |
| 8- to 11-membered bicyclic heteroaryl, such as benzoimidazolium or benzoxazolium | pH > 9 |

The deprotection step can also be carried out during a hair pretreatment step, for instance reducing pretreatment of the hair.

According to one embodiment, the reducing agent is added to the dye composition comprising at least one fluorescent dye of formula (I) or (II) at the time of use.

According to another embodiment, the composition comprising at least one fluorescent dye of formula (I) or (II) also comprises at least one reducing agent as defined above. This composition is then applied to the hair.

According to another embodiment, the reducing agent is applied as a post-treatment, after the application of the composition comprising at least one fluorescent dye of formula (I) or (II). The duration of the post-treatment with the reducing agent may be, for example ranging from 0.1 second to 30 minutes, such as from 1 minute to 15 minutes, with at least one reducing agent as described above. According to another non-limiting embodiment, the reducing agent comprises an agent of thiol or borohydride type as described above.

Another embodiment of the present disclosure relates to a process in which the fluorescent dye of formula (I) or (II) can be applied directly to the hair without reducing agents, free of reducing pretreatment or reducing post-treatment.

A treatment with at least one oxidizing agent may optionally be combined. Any type of oxidizing agent conventional in the field may be used. Thus, the at least one oxidizing agent may be chosen, by way of non-limiting example, from hydrogen peroxide, urea peroxide, alkali metal bromates, persalts such as perborates and persulfates, and also enzymes, among which non-limiting mention may be made of peroxidases, 2-electron oxidoreductases such as uricases and 4-electron oxygenases such as laccases. For example, hydrogen peroxide may be used.

The at least one oxidizing agent can be applied to the fibers before or after the application of the composition comprising at least one fluorescent dye of formula (I) or (II). In one embodiment of the present disclosure, the composition further comprises at least one oxidizing agent.

The application of the dye composition according to the present disclosure can be carried out at ambient temperature. It may, however, be carried out at temperatures ranging from 20 to 180° C.

Another aspect of the present disclosure is also a multi-compartment dyeing device or dyeing "kit" wherein a first compartment comprises a dye composition comprising at least one fluorescent dye of formula (I) or (II) and a second compartment comprising a reducing agent capable of reducing the disulfide functions of keratin materials and/or of the disulfide fluorescent dye of formula (I).

One of these compartments may also comprise at least one other dye of direct dye or oxidation dye type.

The present disclosure also relates to a multicompartment device wherein a first compartment comprises a dye composition comprising at least one fluorescent dye of formula (I) or (II); a second compartment comprises a reducing agent capable of reducing the disulfide bond of keratin materials and/or of the disulfide fluorescent dye of formula (I); and a third compartment comprises an oxidizing agent.

In yet another embodiment, the dyeing device comprises a first compartment comprising a dye composition which comprises at least one protected thiol fluorescent dye of formula (II) and a second compartment comprising an agent capable of deprotecting the protected thiol so as to free the thiol.

Devices described herein may be equipped with a means for delivering the desired mixture to the hair, for example such as the devices described in patent FR 2 586 913.

As disclosed herein, the percentages stated are by weight.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples which follow serve to illustrate the present disclosure without, however, being limiting in nature. The thiol fluorescent dyes of the examples hereinafter have been characterized by conventional spectroscopic and spectrometric methods.

SYNTHESIS EXAMPLES

Example 1

Synthesis of 2,2'-(disulfanediyldiethane-2,1-diyl) bis{5-[4-(dimethylamino)benzylidene]-5,6,7,8-tetrahydroisoquinolinium} dimethane sulfonate [1]

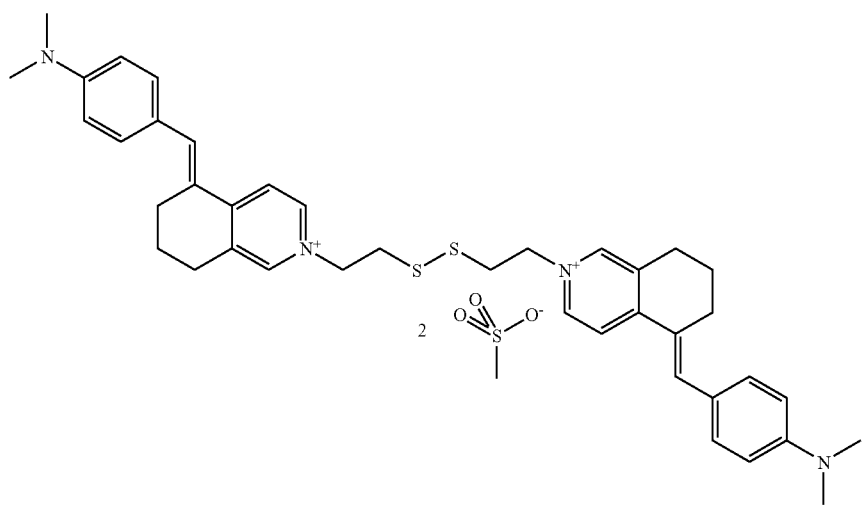

Synthesis scheme

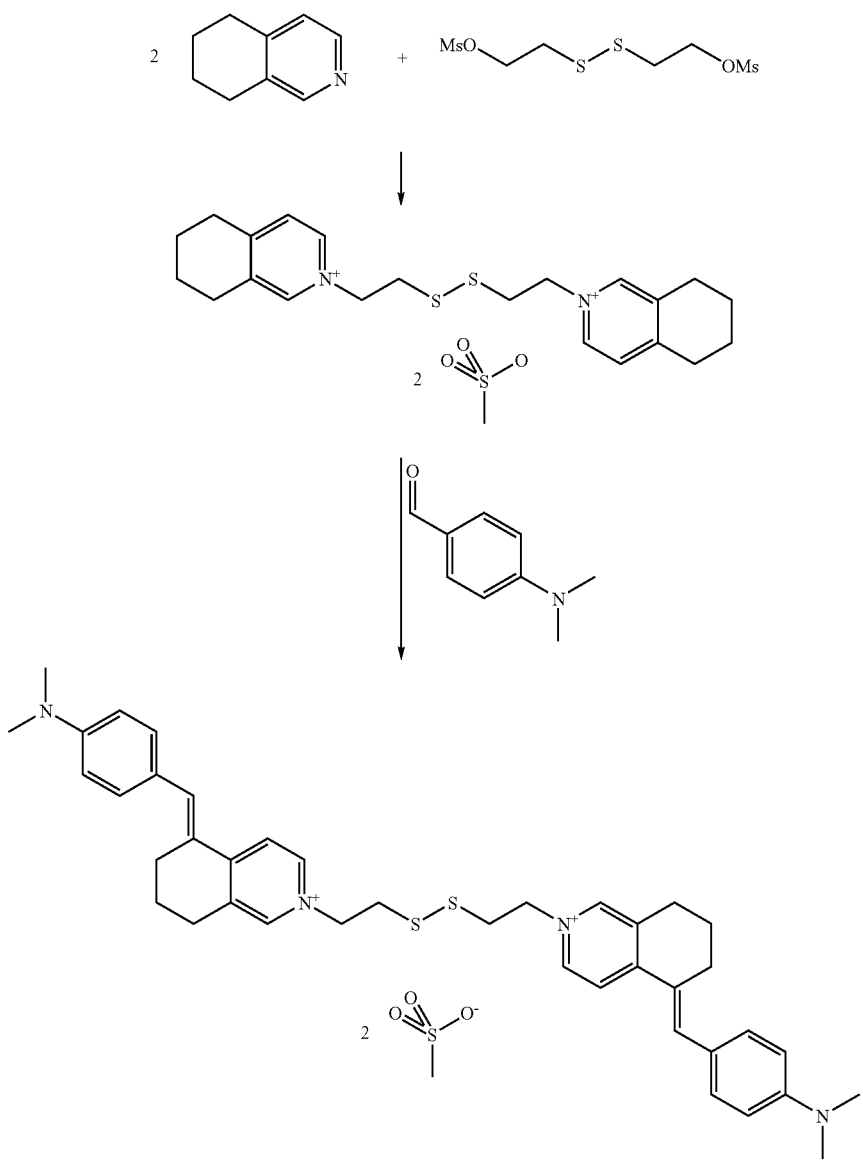

[1]

Stage 1: Synthesis of 2,2'-(disulfanediyldiethane-2,1-diyl)bis(5,6,7,8-tetrahydroisoquinolinium) dimethane sulfonate 3.2 g of 5,6,7,8-tetrahydroisoquinoline and 0.7 g of potassium carbonate were mixed in 3 ml of acetonitrile and brought to 80° C. A solution of 3.4 g of disulfanediyldiethane-2,1-diyl dimethane sulfonate in 3 ml of acetonitrile was added in 10 min. Stirring was maintained for 8 h at 80° C. and then the reaction medium was brought back to ambient temperature, filtered, and concentrated under vacuum. 6 ml of dichloromethane were added and the solution was poured dropwise into 500 ml of ethyl ether. The oil that had been separated by settling out was reprocessed twice by diluting in 6 ml of methanol and adding to 500 ml of ethyl ether, and a final time by diluting in 6 ml of dichloromethane and adding to 500 ml of ethyl ether. After drying under vacuum, 5.2 g of brown solid were recovered. The analyses were in compliance with the expected structure.

Stage 2: 2,2'-(disulfanediyldiethane-2,1-diyl)bis{5-[4-(dimethylamino)benzylidene]-5,6,7,8-tetrahydroisoquinolinium} dimethane sulfonate [1]

2.1 g of 2,2'-(disulfanediyldiethane-2,1-diyl)bis(5,6,7,8-tetrahydroisoquinolinium) dimethane sulfonate and 1.1 g of dimethylaminobenzaldehyde were mixed in 6 ml of methanol. 130 µl of piperidine were added and the mixture is stirred for 8 h at 21° C. 65 µl of piperidine were added and the stirring was maintained for 48 h. 130 µl of piperidine were again added and the mixture was kept stirred for 24 h. The mixture obtained was poured dropwise into 500 ml of methyl-tert-butyl ether with vigorous stirring. A viscous oil separated by settling out. It was separated from the supernatant, diluted in 20 ml of dichloromethane, and poured dropwise into 500 ml of methyl-tert-butyl ether. The orangey-red precipitate formed was filtered off, rinsed with 500 ml of methyl-tert-butyl ether, taken up in 20 ml of dichloromethane, and again poured into 500 ml of methyl-tert-butyl ether, filtered, rinsed, and dried. 2.2 g of red solid are obtained. The analyses showed that it was in compliance.

Example 2

Synthesis of 2,2'-(disulfanediyldibutane-4,1-diyl) bis{5-[(4-methyl-3,4-dihydro-2H-1,4-benzoxazin-7-yl)methylene]-5,6,7,8-tetrahydroisoquinolinium} dimethane sulfonate [2]

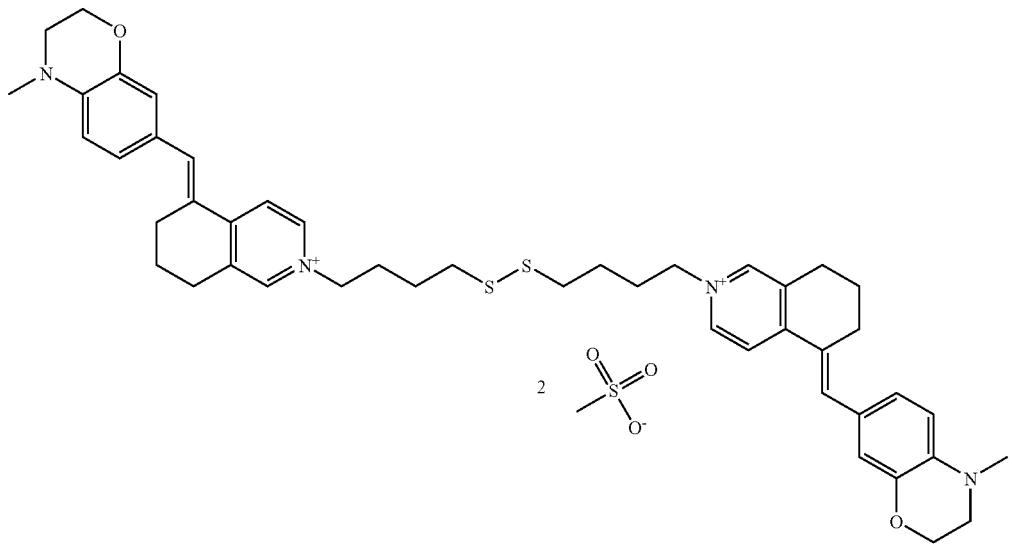

[2]

Synthesis scheme

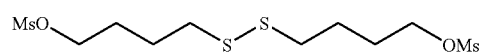

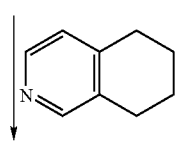

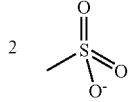

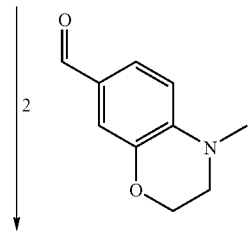

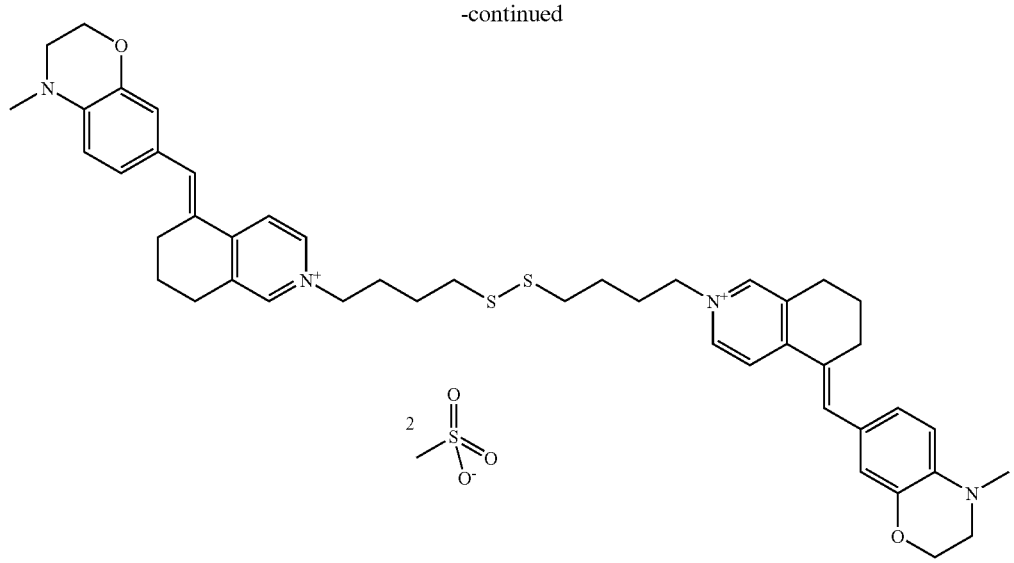

Stage 1: Synthesis of 2,2'-(disulfanediyldibutane-4,1-diyl)bis(5,6,7,8-tetrahydroisoquinolinium) dimethane sulfonate 2.1 g of 5,6,7,8-tetrahydroisoquinoline and 0.5 g of potassium carbonate were mixed in 2 ml of acetonitrile and brought to 100° C. A solution of 2.7 g of disulfanediyldibutane-4,1-diyl dimethane sulfonate in 2 ml of acetonitrile was added in 5 min. Stirring was maintained for 3 h at 100° C. and then the reaction medium was brought back to ambient temperature and concentrated under vacuum. 10 ml of dichloromethane were added and the solution was filtered and then poured dropwise into 100 ml of ethyl ether. The oil that had separated by settling out was reprocessed by diluting in 10 ml of dichloromethane and adding to 500 ml of ethyl ether. After drying under vacuum, 3.3 g of a brown oil were recovered. The analyses were in compliance with the expected structure.

Stage 2: 2,2'-(disulfanediyldibutane-4,1-diyl)bis{5-[(4-methyl-3,4-dihydro-2H-1,4-benzoxazin-7-yl)methylene]-5,6,7,8-tetrahydroisoquinolinium} dimethane sulfonate [2]

2.8 g of 2,2'-(disulfanediyldibutane-4,1-diyl)bis(5,6,7,8-tetrahydroisoquinolinium) dimethane sulfonate and 2 g of 4-methyl-3,4-dihydro-2H-1,4-benzoxazine-7-carbaldehyde were mixed in 28 ml of isopropanol. 0.7 g of piperidine was added and the mixture was stirred for 10 h at 80° C. The mixture was cooled and concentrated under vacuum, taken up in 20 ml of dichloromethane and poured dropwise into 200 ml of ethyl ether. A solid and an oil were formed. They were separated (filtration of the supernatant with the solid), the oil was taken up with 20 ml of dichloromethane, and the mixture was poured into 200 ml of ethyl ether. A new solid fraction was recovered. The solid fractions obtained were each taken up in 20 ml of dichloromethane and concentrated under a strong vacuum. 1.7 g of red solid were recovered. The analyses showed that the product was in compliance with the expected structure.

Example 3

Synthesis of 2,2'-(disulfanediyldiethane-2,1-diyl)bis[5-({4-[bis(2-hydroxyethyl)amino]-phenyl}methylidene)-5,6,7,8-tetrahydroisoquinolinium]bis mesylate[3]

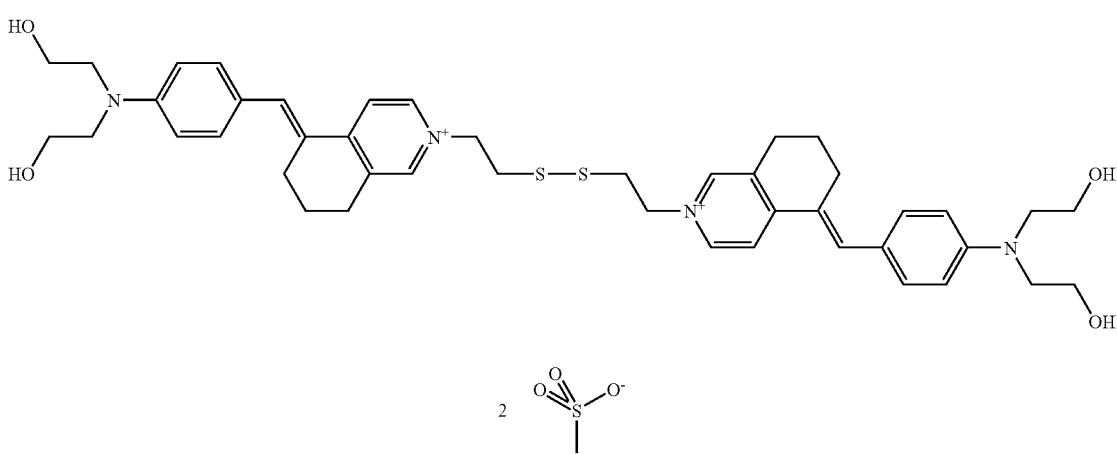

-continued
Synthesis scheme

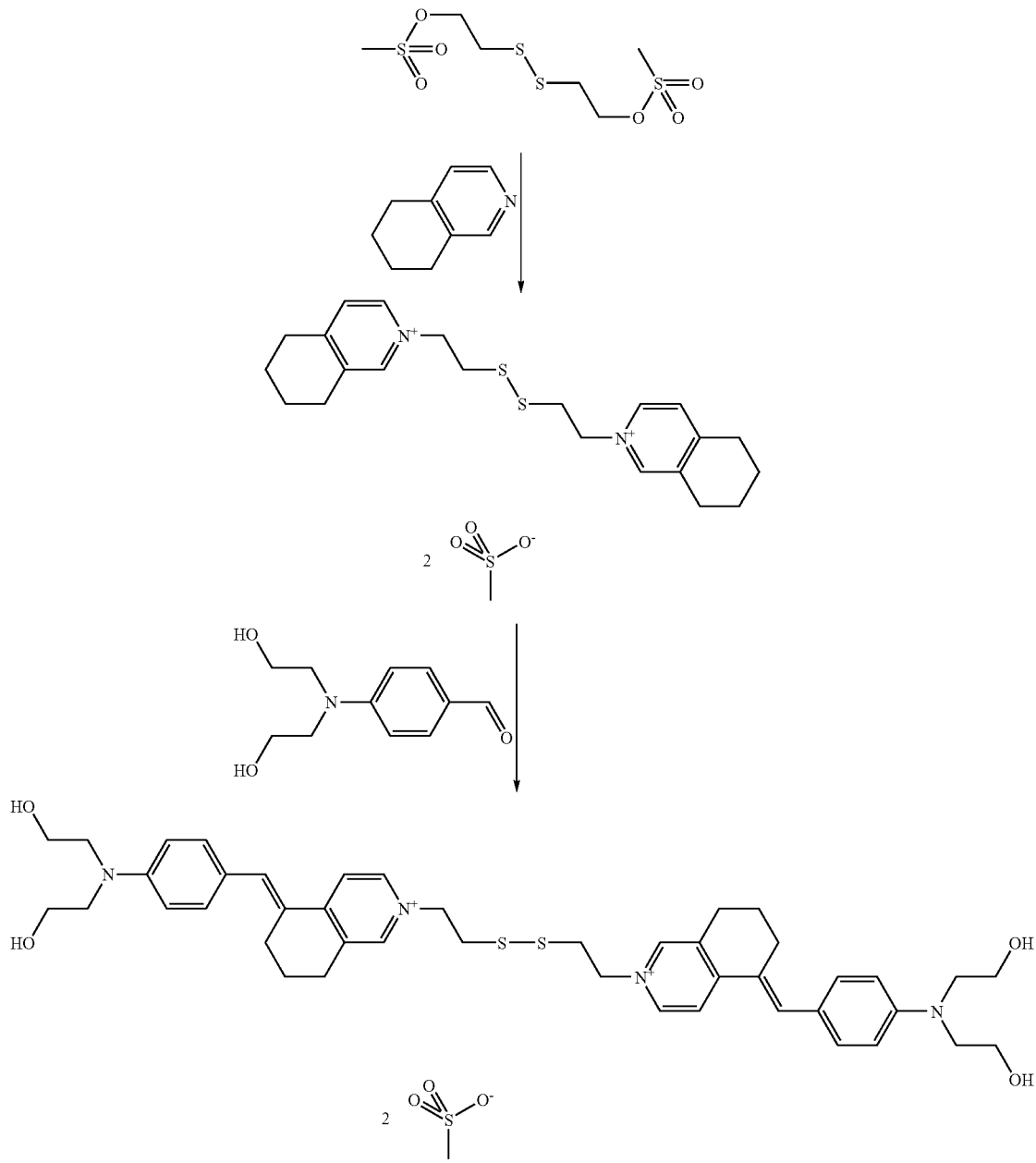

Stage 1: Synthesis of 2,2'-(disulfanediyldiethane-2,1-diyl)di-5,6,7,8-tetrahydroisoquinolinium bis mesylate 50.12 g of disulfanediyldiethane-2,1-diyl dimethanesulfonate were solubilized in 90 mL of N-methylpyrrolidinone (NMP). The mixture was heated at 90° C. and 46.49 g of tetraisoquinoline were added, followed by 50 mL more NMP and 10 mL acetonitrile. After 4 h at 90° C., the reaction mixture was poured on 1.7 L of ethyl acetate (AcOEt) and refrigerated at −10° C. The supernatant solution was discarded, the oil was washed with 100 mL iPrOH and 300 mL diethylether, then several times ethyl acetate until no tetrahydroisoquinoline was detected by TLC. After drying, 77.5 g of oil were collected. Analyses were in accordance with the expected structure and the product was used as such for the following step.

Stage 2: Synthesis of 2,2'-(disulfanediyldiethane-2,1-diyl)bis[5-({4-[bis(2-hydroxyethyl)amino]phenyl}-methylidene)-5,6,7,8-tetrahydroisoquinolinium] bis mesylate 5.12 mL of piperidine were added to a suspension of 45.6 g of 4-[bis-(2-hydroxy-ethyl)-amino]-benzaldehyde and 50 g of 2,2'-(disulfanediyldiethane-2,1-diyl)di-5,6,7,8-tetrahydroisoquinolinium bis mesylate in 200 mL of methanol. After 28 d of mixing at room temperature, the reaction mixture was poured on 1 L ethyl acetate, The sticky dark oil was washed several times with acetone and dried.

Analyses were in accordance with the expected structure of [3].

LC/MS gradient ACONH$_4$ 20 mM->CH$_3$CN 10 min ESI+/−m/z=385; $\lambda_{max}$=468 nm.

NMR 1H (ppm): 1.91 (mH, 4H), 2.69 (s, 6.7H-mesylate), 2.92 (t, 4H), 2.98 (t, 4H), 3.36 (t, 4H), 3.63 (t, 8H), 3.76 (t, 8H), 4.74 (t, 4H), 6.84 (d, 4H), 7.51 (d, 4H), 7.65 (s, 2H), 8.25 (d, 2H), 8.44 (d, 2H), 8.51 (d, 2H).

DYEING EXAMPLES

Example 1

Dyeing Process—Compounds [1] and [2]

Preparation of a Composition A

| Compound [1] or [2] | $5 \times 10^{-4}$ mol % |
|---|---|
| Benzyl alcohol | 4 g |
| Polyethylene glycol 6 EO | 6 g |
| Hydroxyethylcellulose | 0.7 g |
| Alkylpolyglucoside in an aqueous solution containing 65% AM | 4.5 g |
| Demineralized water | qs 100 g |

Preparation of a Composition B

| Thioglycolic acid | 1M |
|---|---|
| Sodium hydroxide | qs pH 8.5 |
| Demineralized water | qs 100 g |

At the time of use, compositions A (9 ml) and B (1 ml) were mixed, then the formulations were applied to locks of natural white hair containing 90% white hairs (NW), permanent-waved white hair (PW), or chestnut-brown hair having a tone height of 4 (TH4). The leave-in time was 20 minutes at ambient temperature AT.

After rinsing with running water, a fixer (Dulcia Vital II®) diluted 10-fold with water was applied for 5 minutes at AT. After rinsing with running water and shampooing, the locks were air-dried and lightening of the dark hair thus treated was observed: the TH4 lock had become visually lighter than untreated control locks. The locks of white hair were colored with strong shades.

Visual Observations:

During the rinsing and shampooing of the colorings obtained with compounds [1] and [2], there was no visible bleeding of the color; the shampoo foam and the rinsing water were virtually uncolored.

The color observed was conserved on the dyed NW and PW, and the lightening effect remained visible on the shampooed TH4 hair.

Reflectance Results for Evaluating the Lightening:

The lightening effectiveness of the compositions in accordance with the present disclosure was expressed as a function of the reflectance of the hair. These reflectances were compared with the reflectance of a lock of untreated hair of tone height TH4 as shown in FIG. 1.

The reflectance was measured by means of a KONIKA-MINOLTA®, CM 3600d spectrophotocolorimeter apparatus and after irradiation of the hair with visible light in the wavelength range of from 400 to 700 nanometers.

It was first of all noted that the reflectance of a lock of hair treated with a composition according to the present disclosure was greater than that of untreated hair. For instance, the reflectance of the locks treated with dyes [1] and [2] was much greater than that of the reference lock in the wavelength range above 560 nm. The locks treated with these two compounds therefore appeared to be lighter.

Results in the L*a*b* System for Evaluating the Coloring of TH4, NW, PW:

The color of the locks was evaluated in the L*a*b* system by means of a MINOLTA® CM 3600D spectrocolorimeter (Illuminant D65).

In this L*a*b* system, L* represents the lightness, a* indicates the green/red color axis and b* the blue/yellow color axis. The higher the value of L, the lighter or weaker the color. Conversely, the lower the value of L, the darker or much stronger the color. The higher the value of a*, the redder the shade, and the higher the value of b*, the more yellow the shade.

The variation in coloring between the TH4 dyed and washed locks of hair was measured by ($\Delta$E) according to the following equation:

$$\Delta E = \sqrt{(L^*-L_o^*)^2+(a^*-a_o^*)^2+(b^*-b_o^*)^2}$$

In this equation, L*, a*, and b* are the values measured before dyeing, and $L_o^*$, $a_o^*$, and $b_o^*$ are the values measured before dyeing (or shampooing).

The greater the value of $\Delta$E, the greater the difference in color between the TH4 locks and the colored locks.

On the TH4 Dark Hair:

| Compounds | L*(D65) | a*(D65) | b*(D65) | $\Delta$E |
|---|---|---|---|---|
| TH4 Reference | 20 | 2.69 | 3.02 | — |
| Compound 1 | 20.53 | 5.72 | 3.84 | 3.19 |
| Compound 2 | 20.12 | 4.92 | 3.7 | 2.34 |

The values reported in the table above show the coloring effect with lightening obtained on the dark hair (TH4) by using compounds 1 and 2.

On the NW and PW Hair:

The natural white hair and the permanent-waved white hair were colored bright orange.

| | L*(D65) | a*(D65) | b*(D65) |
|---|---|---|---|
| Natural white | 60.5 | 1.5 | 16.1 |
| Compound 1 | 39.1 | 37.9 | 33.3 |
| Compound 2 | 35.5 | 36.9 | 29.7 |
| Permanent-waved | | | |
| white | 60.9 | 1.8 | 17.0 |
| Compound 1 | 38.9 | 39.8 | 33.5 |
| Compound 2 | 36.0 | 38.5 | 30.5 |

Fastness with Respect to Successive Shampooing Operations:

The locks treated were divided into two, half were subjected to 5 successive shampooing operations according to a cycle which comprised wetting the locks with water, washing with a conventional shampoo, rinsing with water, followed by drying.

Visual Observations

During the shampooing operations, there was no visible bleeding of the color; the shampoo foam and the rinsing water were not colored.

The color observed and the lightening effect remained visible on the hair of tone height 4 thus treated.

Fastness with Respect to Light:

A study of light-fastness was carried out, by exposure to the Xenotest, on the locks of natural white and permanent-waved white hair for 3 hours. The exposure conditions were 90 W/m², 60% relative humidity and with a chamber temperature of 35° C.

After 3 hours of exposure to the light, the natural white NW hair and the permanent-waved white PW hair dyed with dyes 1 and 2 of the present disclosure were virtually unchanged.

What is claimed is:

1. A fluorescent dye of formula (I) or (II):

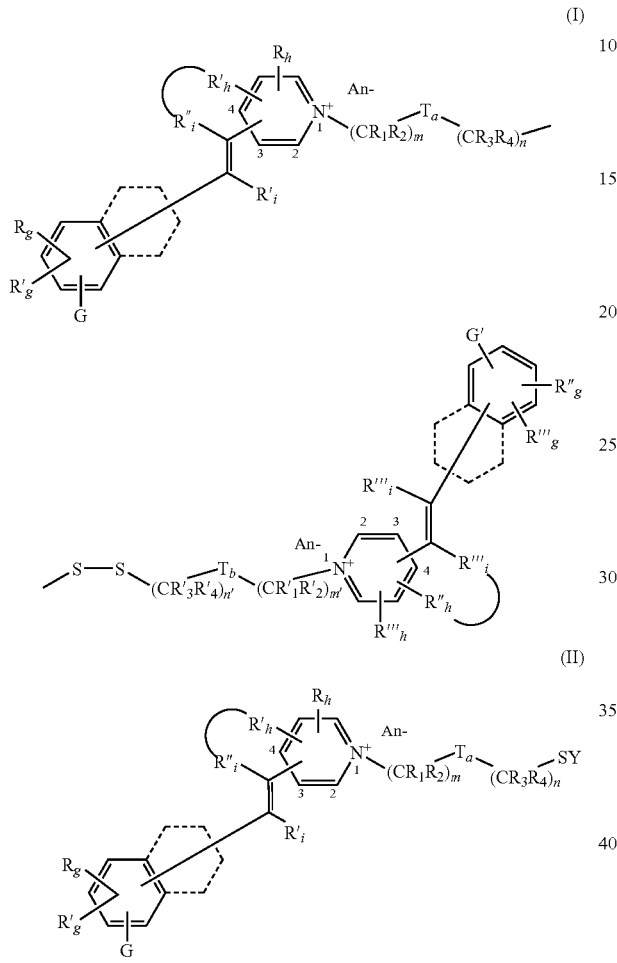

the organic or mineral acid salts thereof, optical isomers and geometric isomers thereof, or the solvates thereof:
wherein:

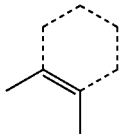

is chosen from an aryl, a heterocyclic, and a heteroaryl group fused to the phenyl ring; or is absent from the phenyl ring;

G and G', which may be identical or different, are chosen from an —$NR_cR_d$ group and a ($C_1$-$C_6$)alkoxy group, which is optionally substituted; or G or G' is absent;

$R_c$ and $R_d$, which may be identical or different, are chosen from a hydrogen atom, an optionally substituted ($C_1$-$C_6$) alkyl group, an aryl($C_1$-$C_4$)alkyl group, and a ($C_1$-$C_6$) alkoxy($C_1$-$C_6$)alkyl group; or the two $R_c$ and $R_d$ radicals may form, together with the nitrogen atoms to which they are attached, a heterocyclic or heteroaryl group;

$R_g$, $R'_g$, $R''_g$, $R'''_g$, $R_h$, and $R''_h$, which may be identical or different, are chosen from a hydrogen atom, a halogen atom, an amino, a (di)($C_1$-$C_4$)alkylamino, a cyano, a carboxyl, a hydroxyl, a trifluoromethyl, a acylamino, a $C_1$-$C_4$ alkoxy, a $C_2$-$C_4$ (poly)hydroxyalkoxy, a ($C_1$-$C_4$) alkylcarbonyloxy, a ($C_1$-$C_4$)alkoxycarbonyl, a ($C_1$-$C_4$) alkylcarbonylamino, a acylamino, a carbamoyl, a ($C_1$-$C_4$)alkylsulfonylamino group, an aminosulfonyl radical, and a ($C_1$-$C_{16}$)alkyl radical optionally substituted with a group chosen from ($C_1$-$C_{12}$)alkoxy, hydroxyl, cyano, carboxyl, amino, and (di)($C_1$-$C_4$)alkylamino wherein optionally the two alkyl radicals borne by the nitrogen atom of the amino group form a heterocycle comprising from 5 to 7 members and optionally comprising another heteroatom identical to or different from that of the nitrogen atom;

or two groups $R_g$ and $R'_g$, or $R''_g$ and $R'''_g$, together with the two adjacent carbon atoms to which they are attached, form a benzo, an indeno ring, a fused heterocycloalkyl, or a fused heteroaryl group; wherein the benzo, indeno, heterocycloalkyl, or heteroaryl ring being optionally substituted with at least one radical chosen from a halogen atom, a ($C_1$-$C_4$)alkyl, an amino, a ($C_1$-$C_4$)alkylamino, a ($C_1$-$C_4$)dialkylamino, a cyano, a carboxyl, a hydroxyl, a trifluoromethyl group, an acylamino, a $C_1$-$C_4$ alkoxy, a $C_2$-$C_4$ (poly)hydroxyalkoxy, a alkylcarbonyloxy, a alkoxycarbonyl, a alkylcarbonylamino, an acylamino, a carbamoyl, a alkylsulfonylamino radical, an aminosulfonyl radical, and a ($C_1$-$C_{16}$) alkyl radical optionally substituted with a group chosen from ($C_1$-$C_{12}$)alkoxy, hydroxyl, cyano, carboxyl, amino, ($C_1$-$C_4$)alkylamino, ($C_1$-$C_4$) dialkylamino, and ($C_1$-$C_4$) dialkylamino wherein the two alkyl radicals borne by the nitrogen atom of the amino group form a heterocycle comprising from 5 to 7 members and optionally comprising another heteroatom identical to or different from that of the nitrogen atom;

or when G and/or G' are —$NR_cR_d$, two groups $R_c$ and $R'_g$, $R_d$ and $R_g$, and/or $R_c$ and $R''_g$, $R_d$ and $R'''_g$ together form a saturated heteroaryl or heterocycle, optionally substituted with at least one ($C_1$-$C_6$)alkyl group;

$R'_i$ and $R'''_i$, which may be identical or different, are chosen from a hydrogen atom and a ($C_1$-$C_4$)alkyl group;

$R'_h$ with $R''_i$ and $R''_h$ with $R'''_i$ form, together with the carbon atoms which bear them, an optionally substituted $C_5$-$C_7$ cycloalkyl group fused to the pyridinium group, wherein the $R'_h$ or $R''_h$ radical and the styryl group bearing the $R'_i$ or $R'''_i$ radical are positioned on adjacent carbon atoms of the pyridinium groups;

$R_1$, $R_2$, $R_3$, $R_4$, $R'_1$, $R'_2$, $R'_3$, and $R'_4$, which may be identical or different, are chosen from:

a hydrogen atom, a ($C_1$-$C_4$)alkyl group, a ($C_1$-$C_{12}$)alkoxy, a hydroxyl, a cyano, a —C(O)O⁻M⁺ wherein M⁺ is an alkali metal or M⁺ and An⁻ are absent, a carboxyl, a (di)($C_1$-$C_4$)(alkyl)amino, wherein the two alkyl radicals may optionally form, with the nitrogen atom which bears them, a heterocycle comprising from 5 to 7 members, optionally comprising another heteroatom which may or may not be different from nitrogen;

$T_a$ and $T_b$, which may be identical or different, are chosen from:

i) a σ covalent bond;

ii) at least one radical or combination thereof, chosen from —$SO_2$—, —O—, —S—, —N(R)—, —N⁺(R) (R°)—, and —C(O)—, wherein R and R°, which may be identical or different, are chosen from a hydrogen atom, a $C_1$-$C_4$ alkyl radical, a $C_1$-$C_4$ hydroxyalkyl radical, and an aryl($C_1$-$C_4$)alkyl; and (iii) a monocyclic, cationic or noncationic, heterocycloalkyl or heteroaryl radical;

m, m', n, and n', which may be identical or different, are integers ranging from 0 to 6, wherein m+n and m'+n', which may be identical or different, are integers ranging from 1 to 10;

An⁻ is an anionic counterion; and

Y is chosen from:
 i) a hydrogen atom;
 ii) an alkali metal;
 iii) an alkaline earth metal;
 iv) an ammonium group: $N^+R^\alpha R^\beta R^\gamma R^\delta$ or a phosphonium group: $P^+R^\alpha R^\beta R^\gamma R^\delta$ wherein $R^\alpha$, $R^\beta$, $R^\gamma$, and $R^\delta$, which may be identical or different, are chosen from a hydrogen atom and a ($C_1$-$C_4$)alkyl group; and
 v) a thiol-function-protecting group;
 wherein when the compound of formula (I) or (II) comprises at least one other cationic part, it is associated with at least one anionic counterion allowing formula (I) or (II) to achieve electroneutrality.

2. The fluorescent dye of formula (II) according to claim 1, wherein Y is chosen from a hydrogen atom and an alkali metal.

3. The fluorescent dye of formula (II) according to claim 1, wherein Y is chosen from a thiol-function-protecting group.

4. The fluorescent dye of formula (II) according to claim 3, wherein Y is chosen from a thiol-function-protecting group chosen from the following radicals:

($C_1$-$C_4$)alkylcarbonyl;
($C_1$-$C_4$)alkylthiocarbonyl;
($C_1$-$C_4$)alkoxycarbonyl;
($C_1$-$C_4$)alkoxythiocarbonyl;
($C_1$-$C_4$)alkylthiothiocarbonyl;
(di)($C_1$-$C_4$)(alkyl)aminocarbonyl;
(di)($C_1$-$C_4$)(alkyl)aminothiocarbonyl;
arylcarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
carboxyl;
$SO_3^-$; $M^+$, wherein $M^+$ is an alkali metal or An⁻ of formula (II) and $M^+$ are absent;
optionally substituted aryl;
optionally substituted heteroaryl;
optionally cationic, optionally substituted heterocycloalkyl,
the following group:

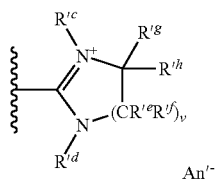

wherein $R'^c$, $R'^d$, $R'^e$, $R'^f$, $R'^g$, and $R'^h$, which may be identical or different, are chosen from hydrogen atoms and ($C_1$-$C_4$) alkyl groups, or two groups $R'^g$ with $R'^h$, and/or $R'^e$ with $R'^f$ form an oxo or thioxo group, or $R'^g$ with $R'^e$ together form a cycloalkyl; and v is an integer ranging from 1 to 3; and An'⁻ is an anionic counterion;

isothiouronium;
—C($NR'^c R'^d$)=$N^+R'^e R'^f$; An'⁻, wherein $R'^c$, $R'^d$, $R'^e$, and $R'^f$, which may be identical or different, are chosen from a hydrogen atom and a ($C_1$-$C_4$)alkyl group, and An⁻ is an anionic counterion;

isothiourea;
—C($NR'^c R'^d$)=$NR'^e$; An'⁻, wherein $R'^c$, $R'^d$, $R'^e$, and An⁻ are defined above;

optionally substituted (di)aryl($C_1$-$C_4$)alkyl;
optionally substituted (di)heteroaryl($C_1$-$C_4$)alkyl;
—$CR^1R^2R^3$, wherein $R^1$, $R^2$, and $R^3$, which may be identical or different, are chosen from:
 i) halogen atom
 ii) ($C_1$-$C_4$)alkyl;
 iii) ($C_1$-$C_4$)alkoxy;
 iv) optionally substituted aryl;
 v) optionally substituted heteroaryl; and
 vi) P($Z^1$)$R'^1 R'^2 R'^3$, wherein $R'^1$ and $R'^2$, which may be identical or different, are chosen from a hydroxyl, a ($C_1$-$C_4$)alkoxy, and a alkyl group; $R'^3$ is chosen from a hydroxyl and a ($C_1$-$C_4$)alkoxy group; and $Z^1$ is chosen from an oxygen atom and a sulfur atom;

a sterically hindered cyclic group; and
optionally substituted alkoxyalkyl.

5. The fluorescent dye of formula (II) according to claim 1, wherein Y is chosen from an alkali metal and a protecting group chosen from:

($C_1$-$C_4$)alkylcarbonyl;
arylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
optionally aryl;
5- or 6-membered cationic monocyclic heteroaryl optionally substituted with at least one ($C_1$-$C_4$)alkyl group which may be identical or different;
8- to 11-membered cationic bicyclic heteroaryl optionally substituted with at least one ($C_1$-$C_4$)alkyl group which may be identical or different;
cationic heterocycle of the following formula:

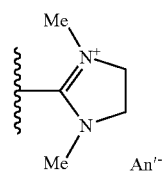

isothiouronium;
—C($NH_2$)=$N^+H_2$; An'⁻;
isothiourea;
—C($NH_2$)=NH; and
$SO_3^-$; $M^+$, wherein $M^+$ is an alkali metal or An⁻ of formula (II) and $M^+$ are absent.

6. The fluorescent dye of formula (I) according to claim 1, comprising a C2 axis of symmetry between the two sulfur atoms of the central disulfide radical.

7. The fluorescent dye according to claim 1, comprising at least one of the two formulae (Ia) and (IIa):

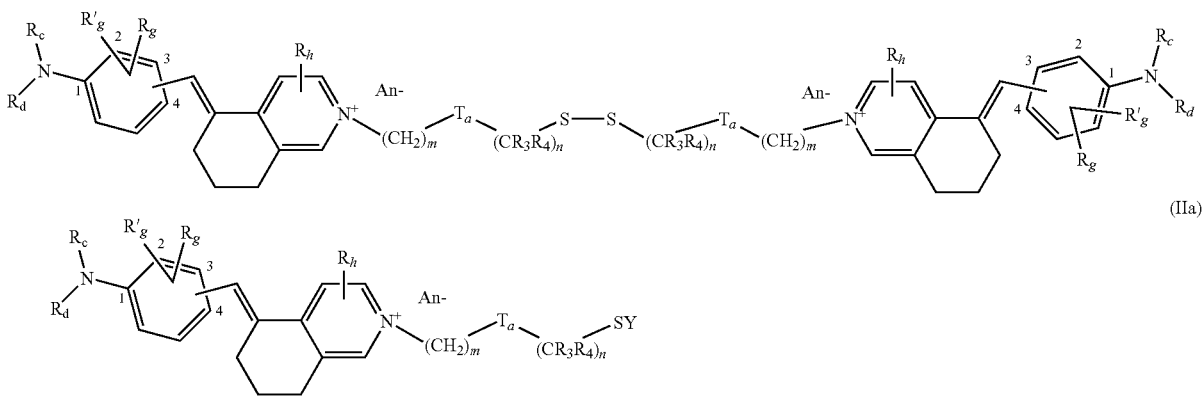

wherein:
R$_3$ and R$_4$, which may be identical or different, are chosen from:
- a hydrogen atom;
- a (C$_1$-C$_4$)alkyl group;
- a —C(O)O$^-$M$^+$, wherein M$^+$ is an alkali metal, or M$^+$ and An$^-$ are absent;
- carboxyl;

R$_g$, R'$_g$, and R$_h$, which may be identical or different, are chosen from a hydrogen atom, a halogen atom, a (di)(C$_1$-C$_4$)(alkyl)amino, a hydroxyl, an acylamino, a (C$_1$-C$_4$)alkoxy group, a (C$_1$-C$_4$)alkylcarbonylamino group, and a (C$_1$-C$_6$)alkyl radical;

two groups R$_c$ and R'$_g$ and/or R$_d$ and R$_g$ together form a saturated heterocycle or a heteroaryl, optionally substituted with at least one (C$_1$-C$_6$)alkyl group;

R$_c$ and R$_d$, which may be identical or different, are chosen from a hydrogen atom, an optionally substituted (C$_1$-C$_6$) alkyl group, and an aryl(C$_1$-C$_4$)alkyl;

or the two radicals R$_c$ and R$_d$, together with the nitrogen atoms to which they are attached, form a heterocyclic or heteroaryl group;

T$_a$ is chosen from a σ covalent bond and a group chosen from: —N(R)—, —C(O)—N(R)—, and N(R)—C(O)—;

m and n, which may be identical or different, are chosen from an integer ranging from 1 to 6, wherein the sum m+n is an integer ranging from 2 to 6;

An$^-$ is an anionic counterion; and

Y is as defined in claim 1;

wherein, when the compounds of formula (Ia) or (IIa) comprise other cationic parts, they are associated with at least one anionic counterion allowing formula (Ia) or (IIa) to achieve electroneutrality.

8. The fluorescent dye according to claim 1, chosen from one of the following formulae:

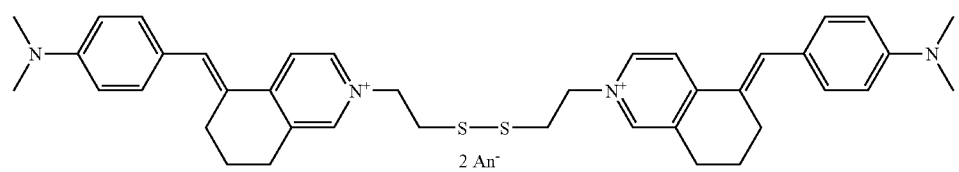

1

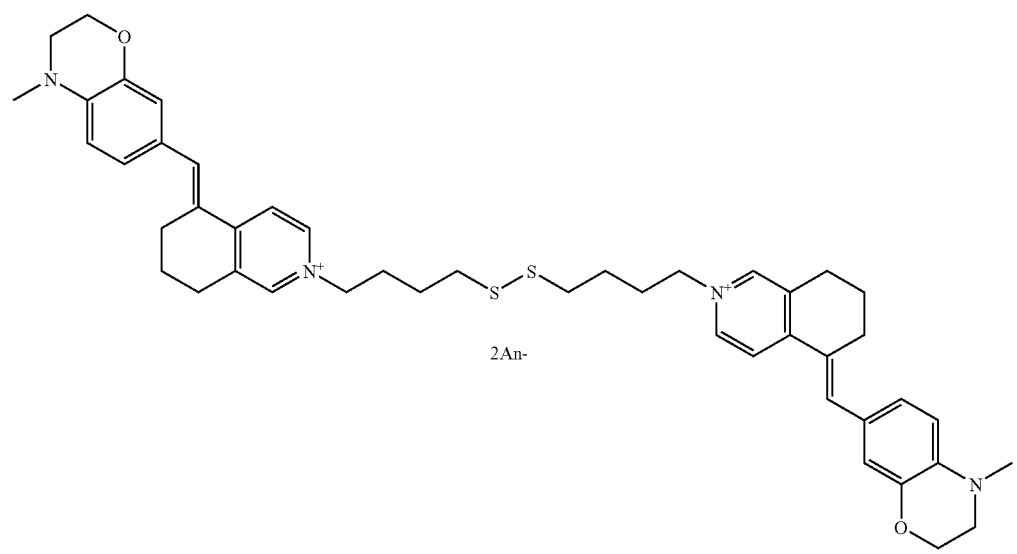

2

-continued
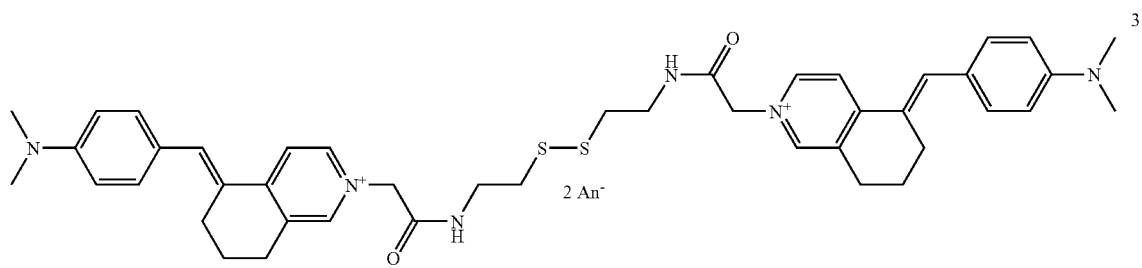
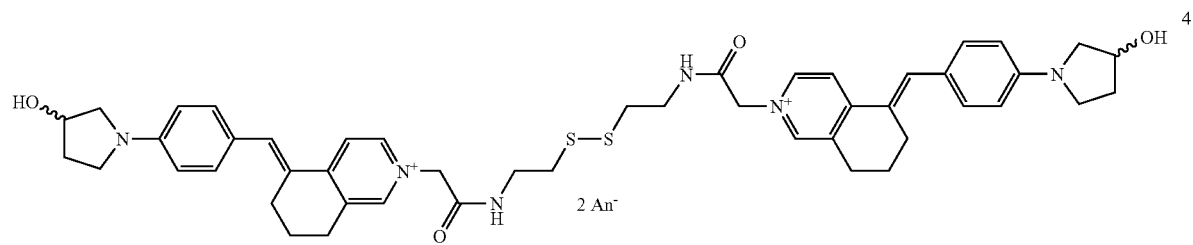
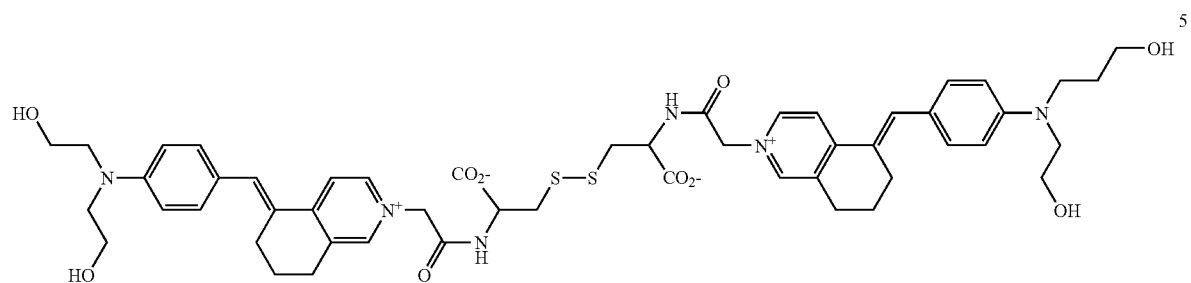
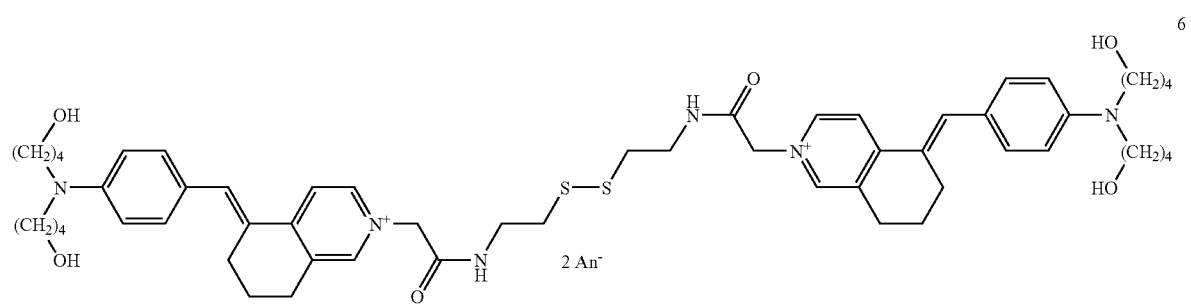
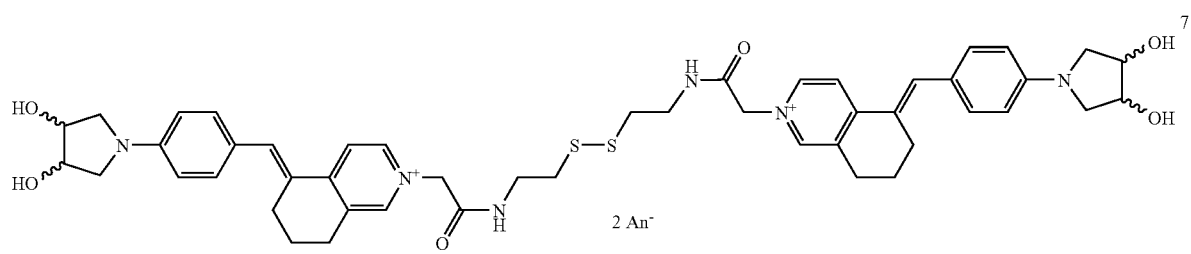
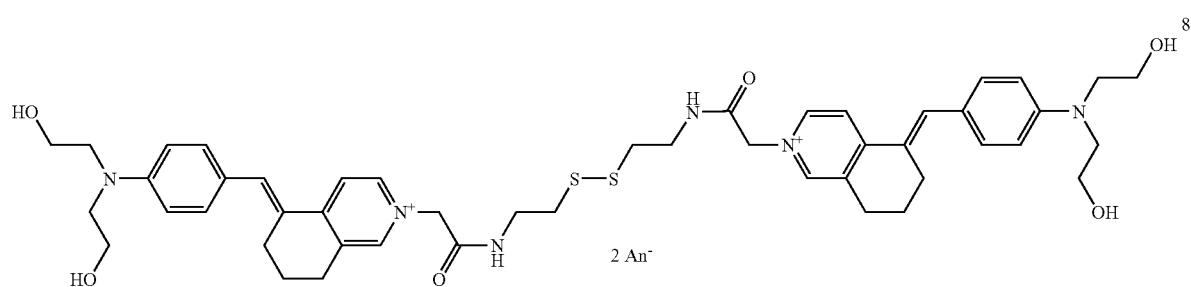

-continued
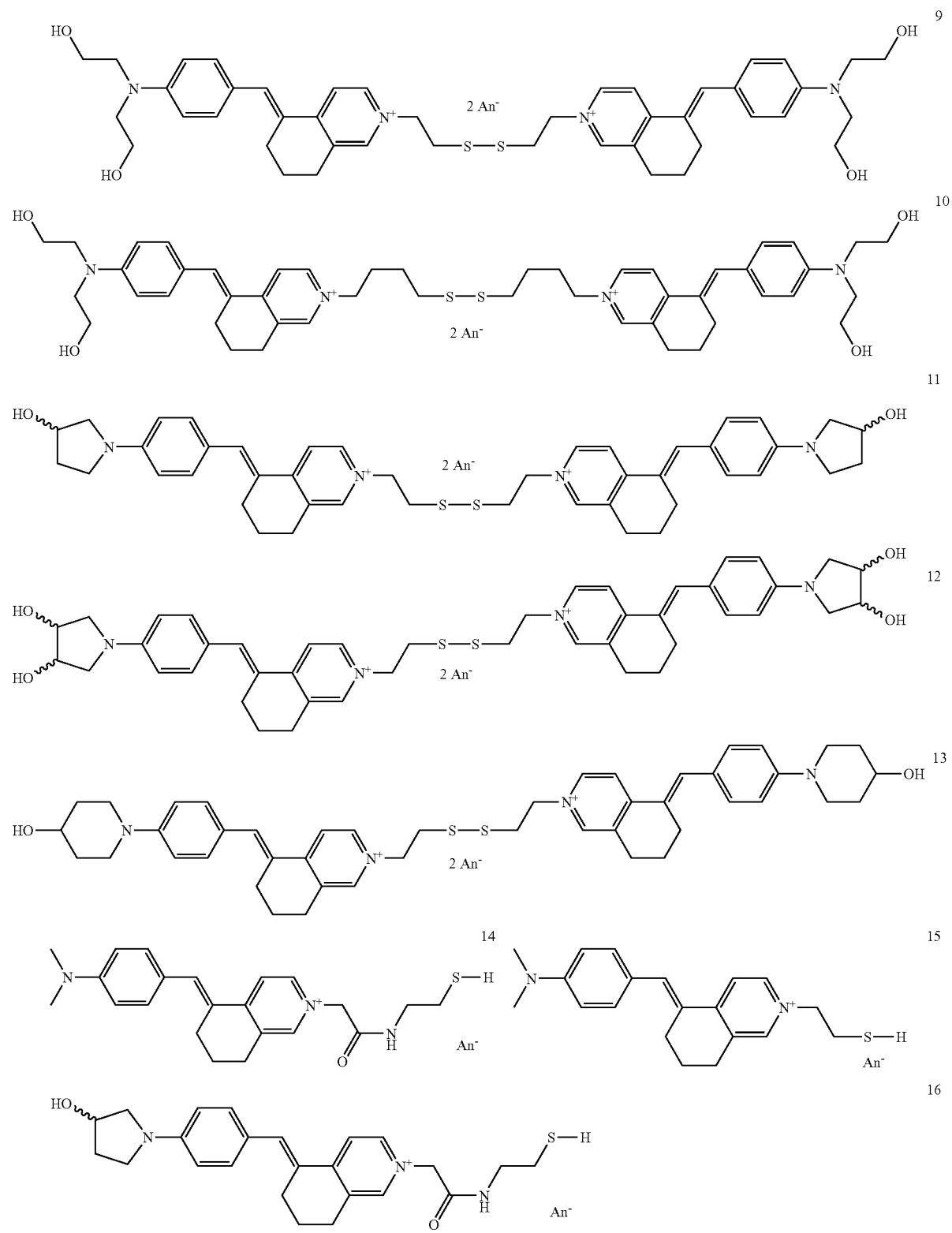

-continued
17
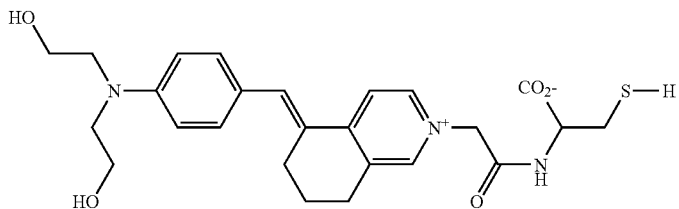
18
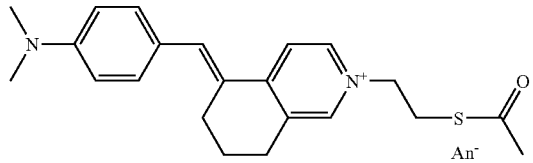
19
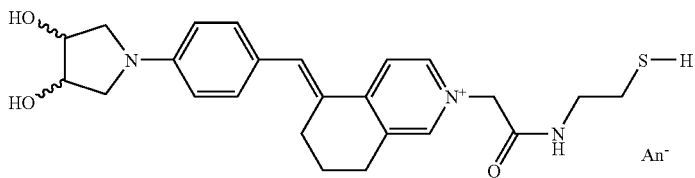
20
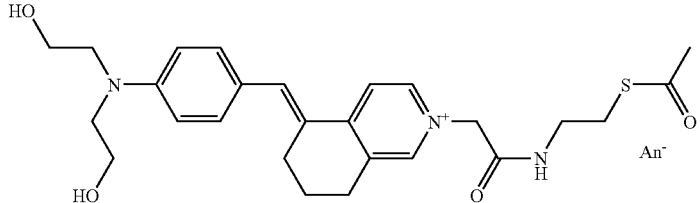
21
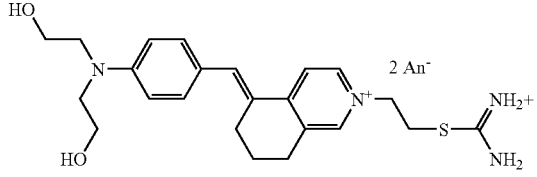
22
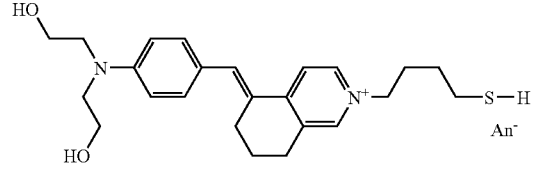
23
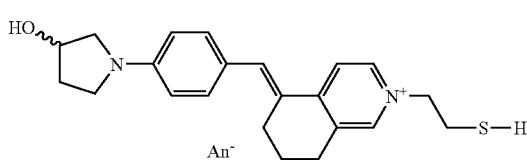
24
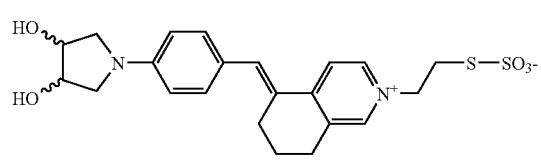
25
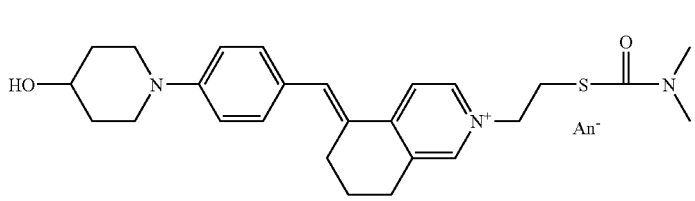
26
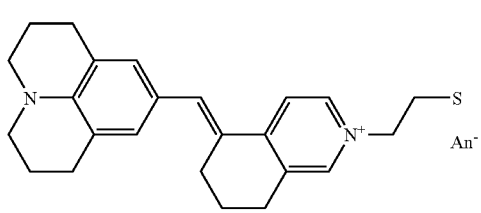
27
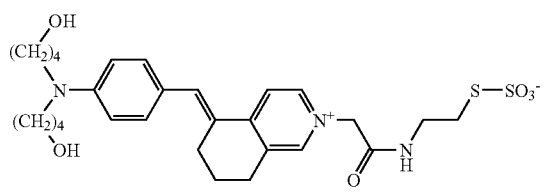

-continued

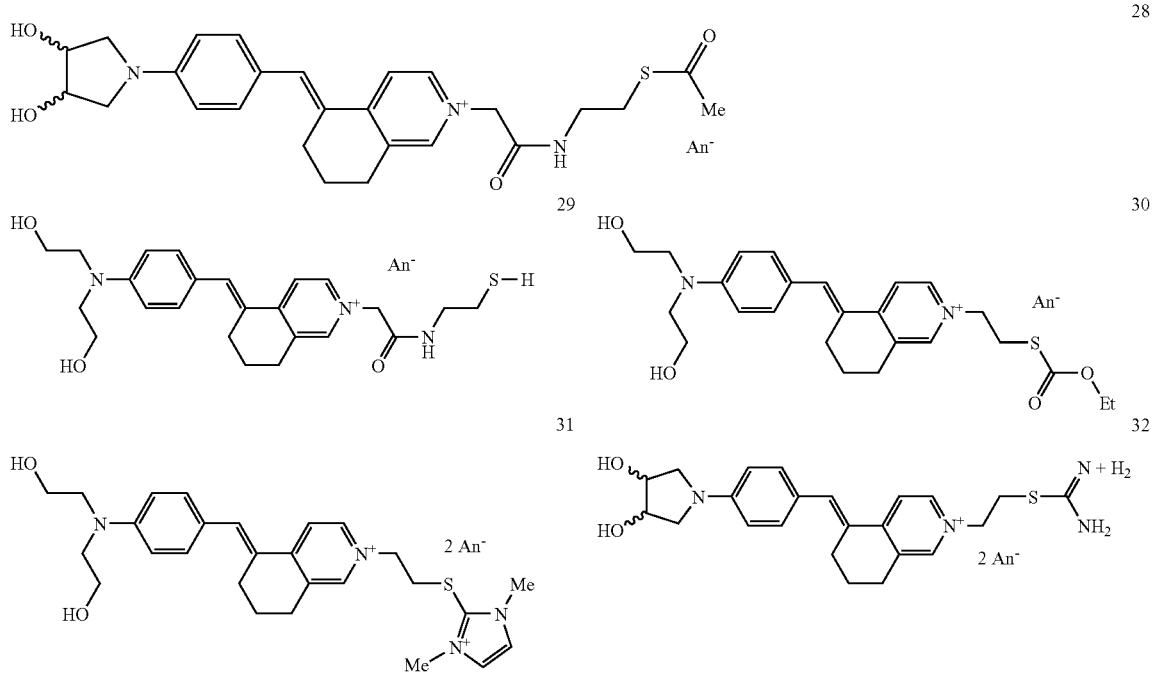

wherein An⁻, which may be identical or different, is chosen from an anionic counterion.

9. A dye composition, comprising, in a cosmetically acceptable medium, at least one fluorescent dye of formula (I) or (II) according to claim 1.

10. A process for dyeing keratin materials, comprising applying to the keratin materials a dye composition comprising at least one fluorescent dye of formula (I) or (II) according to claim 1, optionally in the presence of a reducing agent.

11. The process for dyeing keratin materials according to claim 10, wherein said keratin materials are dark human keratin fibers.

12. The process for dyeing keratin materials according to claim 10, wherein the keratin materials are dark keratin fibers comprising a tone height of less than or equal to 6.

13. The process for dyeing keratin materials according to claim 12, wherein said dark human keratin fibers comprise a tone height of less than 6.

14. The process for dyeing keratin materials according to claim 10, wherein said dark human keratin fibers are lightened.

15. The process for dyeing keratin materials according to claim 10, further comprising applying an oxidizing agent to the keratin fibers.

16. A multicompartment device comprising a first compartment and a second compartment, wherein the first compartment comprises a dye composition comprising at least one fluorescent dye of formula (I) or (II) according to claim 1, and the second compartment comprises a reducing agent.

17. The multicompartment device according to claim 16, further comprising a third compartment comprising an oxidizing agent.

* * * * *